United States Patent
Jung et al.

(10) Patent No.: US 11,555,797 B2
(45) Date of Patent: Jan. 17, 2023

(54) SEMICONDUCTOR-TYPE BATTERY-FREE GAS SENSOR OR HUMIDITY SENSOR INCLUDING POROUS METAL-ORGANIC FRAMEWORK AND METHOD OF MANUFACTURING THE SAME

(71) Applicant: GWANGJU INSTITUTE OF SCIENCE AND TECHNOLOGY, Gwangju (KR)

(72) Inventors: Gun Young Jung, Seoul (KR); Hyeonghun Kim, Jeju-si (KR)

(73) Assignee: GWANGJU INSTITUTE OF SCIENCE AND TECHNOLOGY

( * ) Notice: Subject to any disclaimer, the term of this patent is extended or adjusted under 35 U.S.C. 154(b) by 364 days.

(21) Appl. No.: 15/930,414

(22) Filed: May 12, 2020

(65) Prior Publication Data

US 2020/0400604 A1 Dec. 24, 2020

(30) Foreign Application Priority Data

Jun. 24, 2019 (KR) .......................... 10-2019-0075075

(51) Int. Cl.
  *G01N 27/22* (2006.01)
  *G01N 27/12* (2006.01)
  *G01N 33/00* (2006.01)

(52) U.S. Cl.
  CPC ......... *G01N 27/223* (2013.01); *G01N 27/129* (2013.01); *G01N 27/227* (2013.01);
  (Continued)

(58) Field of Classification Search
  CPC ............. G01N 2027/222; G01N 21/77; G01N 21/783; G01N 21/81; G01N 27/129;
  (Continued)

(56) References Cited

U.S. PATENT DOCUMENTS

2017/0003272 A1* 1/2017 Kim ..................... B01J 35/0033
2017/0333842 A1* 11/2017 Robinson ............. B01J 35/1014
2019/0011412 A1* 1/2019 Jung ...................... H01L 21/28

FOREIGN PATENT DOCUMENTS

KR      101269510 B1 *  5/2013   ........... G01N 27/127
KR      101507538 B1 *  4/2015   ............. G01N 27/02
(Continued)

*Primary Examiner* — Alvaro E Fortich
*Assistant Examiner* — Dilara Sultana
(74) *Attorney, Agent, or Firm* — Renaissance IP Law Group LLP

(57) ABSTRACT

The present inventive concept relates to a battery-free gas sensor or humidity sensor comprising a metal-organic framework and a method of manufacturing the same. In a photodiode-type battery-free gas sensor or humidity sensor according to the present inventive concept, since photoelectron collection electrodes are formed at certain intervals between P-N junction layers, when gas is adsorbed thereon, the gas can be detected without an extra power source by change of photocurrent. Due to fine pores of the metal-organic framework, gas sensitivity may be increased and stability of catalysts may be improved. When catalysts are not provided, humidity may be detected. Therefore, a system that used the photodiode-type battery-free gas sensor and the photodiode-type battery-free humidity sensor together may be performed humidity correction to accurately measure an amount of a gas.

18 Claims, 18 Drawing Sheets

(52) U.S. Cl.
CPC ..... *G01N 33/0037* (2013.01); *G01N 33/0044* (2013.01); *G01N 2027/222* (2013.01)

(58) Field of Classification Search
CPC ............... G01N 27/223; G01N 27/227; G01N 33/0037; H01L 21/02205; H01L 29/66136
See application file for complete search history.

(56) References Cited

FOREIGN PATENT DOCUMENTS

| | | | | | |
|---|---|---|---|---|---|
| KR | 20180055117 | A | * | 5/2018 | ........... G01N 27/129 |
| KR | 20180055117 | A | | 5/2018 | |
| KR | 20180070067 | A | * | 6/2018 | ........... G01N 27/327 |

* cited by examiner

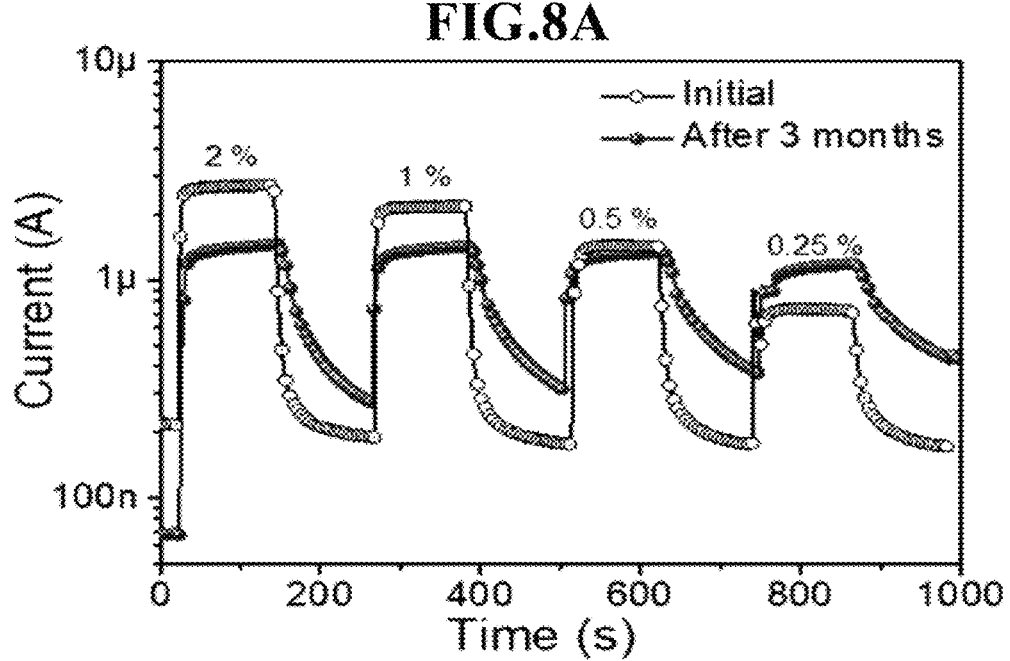

SEMICONDUCTOR-TYPE BATTERY-FREE GAS SENSOR OR HUMIDITY SENSOR INCLUDING POROUS METAL-ORGANIC FRAMEWORK AND METHOD OF MANUFACTURING THE SAME

CLAIM FOR PRIORITY

This application claims priority to Korean Patent Application No. 2019-0075075 filed on Jun. 24, 2019 in the Korean Intellectual Property Office (KIPO), the entire contents of which are hereby incorporated by reference.

BACKGROUND

1. Technical Field

Embodiments of the present disclosure relate to a semiconductor-type battery-free gas sensor or humidity sensor, and more particularly, to a semiconductor-type battery-free gas sensor or humidity sensor comprising a porous metal-organic framework and a method of manufacturing the same.

2. Related Art

Gas sensors are elements that may measure a concentration of a specific gas (target gas) in real time and have been manufactured as various types of gas sensors such as electrochemical-type gas sensors, contact combustion-type gas sensors, and semiconductor-type gas sensors. Among the gas sensors, the semiconductor-type gas sensor using an oxide, of which resistance is changed according to a concentration of a target gas, may be miniaturized, and thus, the semiconductor-type gas sensor may be applied as a next-generation sensor for Internet of Things (IoT).

The semiconductor-type gas sensor uses a chemical interaction between an air component and a semiconductor surface, and thus, heating is essentially required. For example, oxygen is pre-adsorbed onto a heated semiconductor surface, and when the semiconductor surface is exposed to a specific gas and the gas and the pre-adsorbed oxygen react with each other to change a surface adsorbate, density of electrons in a semiconductor is changed. Heating is performed to detect a specific gas through a corresponding process, and a heating temperature of the heating is changed according to a type of gas to be detected.

The heating is generally performed at a temperature ranging from 200° C. to 800° C. However, the semiconductor-type gas sensor essentially requiring the heating, since a high temperature should be applied, it is difficult to perform repetitive measurement, and since a heating portion and an electrode portion need to be installed respectively, a structure is complicated, and a gas detection process is complicated.

Meanwhile, recently, research has been conducted on P-N diode-type battery-free gas sensors capable of detecting gas molecules without an external power source. When light is irradiated onto the battery-free gas sensor, a short circuit current flows through a P-N diode, and when gas molecules (for example, $NO_2$ as an oxidizing gas or $NH_3$ as a reducing gas) are exposed to a two-dimensional material in the composition of the P-N diode, a change in the short circuit current value occurs. The battery-free gas sensor may detect gas molecules through the change in the value of the short circuit current.

As the conventional battery-free gas sensor, Korean Patent Publication No. 10-2018-0055117 discloses "BATTERY-FREE GAS SENSOR USING TWO-DIMENSIONAL TRANSITION METAL COMPOUND-BASED PN DIODE AND METHOD OF MANUFACTURING THE SAME." Specifically, disclosed is a battery-free gas sensor manufactured by forming a p-type semiconductor and an n-type semiconductor on a substrate on which a first electrode is formed by using a transition metal dichalcogenide material and forming a second electrode. However, the gas sensor is difficult to synthesize and expensive due to use of an expensive two-dimensional transition metal and has low sensitivity. In addition, since additional catalysts are not introduced, the gas sensor cannot detect hydrogen or the like.

Furthermore, since metal catalysts currently introduced to induce smooth adsorption and desorption of gases at the time of manufacturing semiconductor-type gas sensors are very fine catalysts with a size of 2 nm to 5 nm, the catalysts aggregate with each other or pollutants (organic materials, fine dust, oil, etc.) are adsorbed on the sensor. Thus, when the sensor is used for a long time, performance of the sensor is continuously degraded. In addition, when moisture is attached to a surface of the catalyst, performance of the sensor is degraded, and thus, the performance of the gas sensor may be changed according to humidity. Therefore, there is a need for a new method capable of stably maintaining performance of corresponding catalysts.

Accordingly, the present inventors have conducted research into stably maintaining performance of catalysts and improving sensitivity of a sensor and thus have found that, when a porous metal-organic framework layer is formed on a gas adsorption layer comprising catalysts, the catalysts may be protected and a target gas may aggregate to improve sensitivity of a sensor, and since the porous metal-organic framework layer itself may absorb vapor in the air to detect humidity, the sensor may be used as a humidity sensor when the sensor does not include the catalysts, thereby completing the present inventive concept.

SUMMARY

Accordingly, example embodiments of the present inventive concept are provided to substantially obviate one or more problems due to limitations and disadvantages of the related art.

Example embodiments of the present inventive concept provide a new semiconductor-type battery-free gas sensor having high sensitivity.

Example embodiments of the present inventive concept provide a method of manufacturing the semiconductor-type battery-free gas sensor.

Example embodiments of the present inventive concept provide a semiconductor-type battery-free humidity sensor.

Example embodiments of the present inventive concept provide a method of manufacturing the semiconductor-type battery-free humidity sensor.

Example embodiments of the present inventive concept provide a semiconductor-type battery-free gas sensor system in which an influence of humidity is corrected.

In some example embodiments, a photodiode-type battery-free gas sensor includes a semiconductor substrate, a first insulator layer for an upper electrode which is formed on a part of an upper portion of the semiconductor substrate, a second insulator layer which is formed on a part of the substrate, formed partially in contact with the first insulator layer, formed in a direction perpendicular to a length direction of the first insulator layer, and formed with linear patterns spaced apart from each other by a certain interval, photoelectron collection electrodes which are formed on the first insulator layer and the second insulator layer and form linear patterns in the same direction as the second insulator layer, a semiconductor oxide layer which covers a portion or an entirety of each of the photoelectron collection electrodes formed with the linear patterns on the second insulator layer and covers the semiconductor substrate positioned between the linear patterns, metal nanoparticle catalysts formed on the semiconductor oxide layer, a metal-organic framework layer formed to cover the semiconductor oxide layer and the metal nanoparticle catalysts, an upper electrode which covers a portion of each of the photoelectron collection electrodes formed on the first insulator layer so as to be connected to the photoelectron collection electrodes, and a lower electrode in contact with a lower portion of the semiconductor substrate.

When the semiconductor substrate is made of a p-type semiconductor material, the semiconductor oxide layer may be made of an n-type semiconductor material, and when the semiconductor substrate is made of an n-type semiconductor material, the semiconductor oxide layer may be made of a p-type semiconductor material.

The p-type semiconductor material can be applied to a substrate and may be p-type silicon or indium gallium nitride, and the n-type semiconductor material can be applied as a semiconductor oxide and may be selected from the group consisting of indium gallium zinc oxide (IGZO), zinc oxide (ZnO), tin oxide ($SnO_2$), and titanium dioxide ($TiO_2$).

The first insulator layer and the second insulator layer may be made of silicon oxide or aluminum oxide.

The first insulator layer and the second insulator layer may have a thickness ranging from 50 nm to 200 nm.

The interval between the linear patterns of the second insulator layer and the photoelectron collection electrodes may be in a range of 5 μm to 30 μm.

When a hydrogen gas is detected, a palladium (Pd) catalyst may be used as the metal nanoparticle catalyst, when an $NO_2$ gas is detected, a nickel (Ni) catalyst may be used as the metal nanoparticle catalyst, and when an $H_2S$ gas is detected, a copper (Cu) catalyst may be used as the metal nanoparticle catalyst.

A metal constituting the metal-organic framework layer may be selected from the group consisting of iron, aluminum, zinc, chromium, zirconium, and copper.

A metal-organic framework constituting the metal-organic framework layer may have a specific surface area ranging from 100 $m^2/g$ to 4,300 $m^2/g$.

A metal-organic framework constituting the metal-organic framework layer may have a density ranging from 0.1 $g/cm^3$ to 1.0 $g/cm^3$.

A metal-organic framework used in the metal-organic framework layer may be selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate).

In other example embodiments, a method of manufacturing a photodiode-type battery-free gas sensor includes a) forming a first insulator layer for an upper electrode on a part of an upper portion of a semiconductor substrate, b) forming a stacked structure of photoelectron collection electrodes and a second insulator layer, which are formed with linear patterns spaced apart from each other by a certain interval, on the upper portion of the semiconductor substrate comprising the first insulator layer, c) forming a semiconductor oxide layer which covers the stacked structure of the photoelectron collection electrodes and the second insulator layer, d) forming metal nanoparticle catalysts on the semiconductor oxide layer, e) forming a metal-organic framework layer which covers the semiconductor oxide layer and the metal nanoparticle catalysts, f) forming an upper electrode which covers the photoelectron collection electrodes formed on the first insulator layer, and g) forming a lower electrode below the semiconductor substrate.

The first insulator layer and the second insulator layer may be made of silicon oxide or aluminum oxide.

The linear patterns of the stacked structure of the photoelectron collection electrodes and the second insulator layer may be formed through photolithography.

A metal-organic framework used in the metal-organic framework layer may be selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate).

In still other example embodiments, a photodiode-type battery-free humidity sensor includes a semiconductor substrate, a first insulator layer for an upper electrode formed on a part of an upper portion of the semiconductor substrate, a second insulator layer which is formed on a part of the substrate, formed partially in contact with the first insulator layer, formed in a direction perpendicular to a length direction of the first insulator layer, and formed with linear patterns spaced apart from each other by a certain interval, photoelectron collection electrodes which are formed on the first insulator layer and the second insulator layer and form linear patterns in the same direction as the second insulator layer, a semiconductor oxide layer which covers a portion or an entirety of each of the photoelectron collection electrodes formed with the linear patterns on the second insulator layer and covers the semiconductor substrate positioned between the linear patterns, a metal-organic framework layer which covers the semiconductor oxide layer, an upper electrode which covers a portion of each of the photoelectron collection electrodes formed on the first insulator layer so as to be connected to the photoelectron collection electrodes, and a lower electrode in contact with a lower portion of the semiconductor substrate.

In yet other example embodiments, a method of manufacturing a photodiode-type battery-free moisture sensor includes a) forming a first insulator layer for an upper electrode on a part of an upper portion of a semiconductor substrate, b) forming a stacked structure of photoelectron collection electrodes and a second insulator layer, which are formed with linear patterns spaced apart from each other by a certain interval, on the upper portion of the semiconductor substrate comprising the first insulator layer, c) forming a semiconductor oxide layer which covers the stacked structure of the photoelectron collection electrodes and the second insulator layer, d) forming a metal-organic framework layer which covers the semiconductor oxide layer, e) forming an upper electrode which covers the photoelectron collection electrodes formed on the first insulator layer, and g) forming a lower electrode below the semiconductor substrate.

In yet other example embodiments, a photodiode-type battery-free gas sensor system includes the photodiode-type battery-free gas sensor and the photodiode-type battery-free humidity sensor.

BRIEF DESCRIPTION OF DRAWINGS

Example embodiments of the present inventive concept will become more apparent by describing example embodiments of the present inventive concept in detail with reference to the accompanying drawings, in which:

FIG. 8A is a graph showing hydrogen gas detection performance when a photodiode-type battery-free gas sensor according to one Comparative Example of the present inventive concept performs initial measurement and measurement after 3 months;

DESCRIPTION OF EXAMPLE EMBODIMENTS

Figure 1:
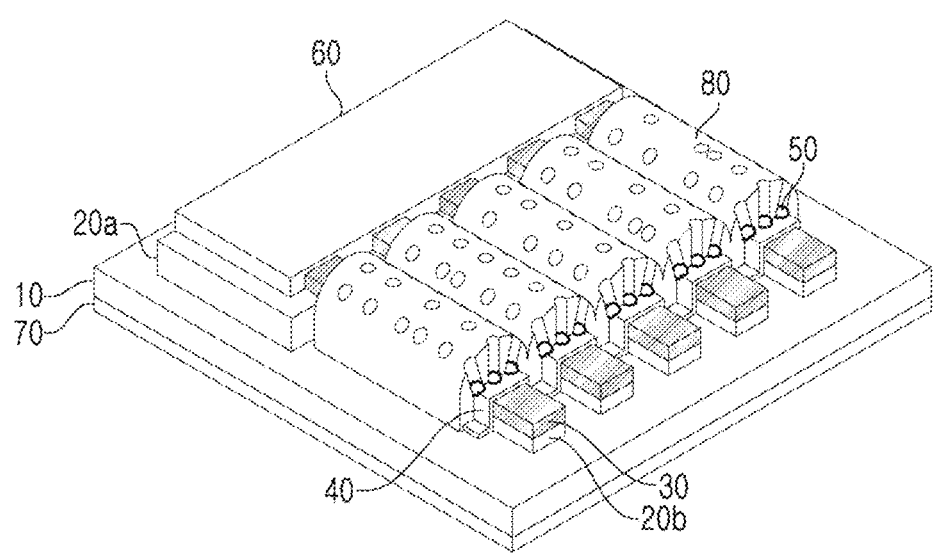
FIG. 1 is a schematic diagram of a photodiode-type battery-free gas sensor according to one example embodiment of the present inventive concept.

Hereinafter, example embodiments and examples of the present inventive concept will be described in detail with reference to the accompanying drawings so that the present inventive concept may be readily implemented by those skilled in the art.

However, it is to be noted that the present inventive concept is not limited to the described example embodiments and examples but may be embodied in various different forms. In the drawings, certain parts not directly relevant to the description are omitted to enhance the clarity of the present inventive concept, and like reference numerals denote like parts throughout the whole specification.

Throughout the specification, when an element "includes" a component, it may indicate that the element does not exclude another component but can further include another component unless otherwise stated.

Photodiode-Type Battery-free Gas Sensor Hereinafter, a photodiode-type battery-free gas sensor according to one example embodiment of the present inventive concept will be described in detail with reference to FIGS. 1 and 2.

Figure 2:
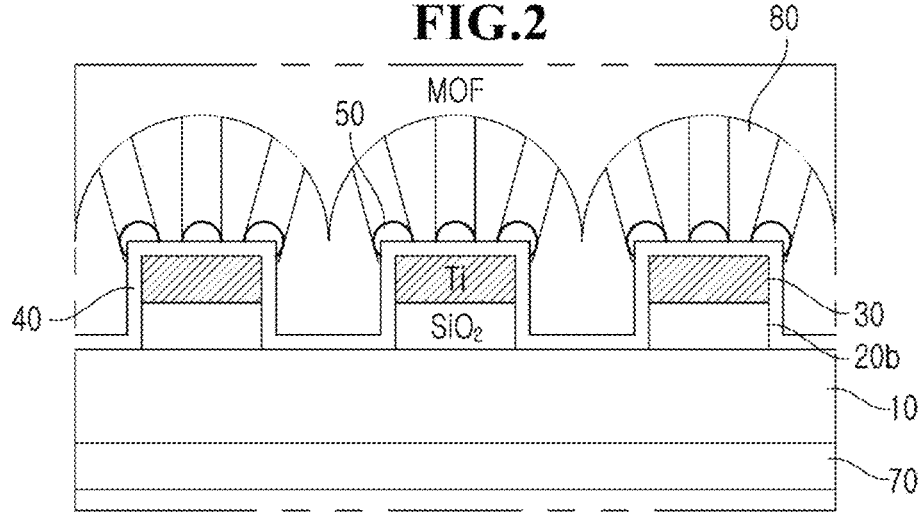
FIG. 2 is a cross-sectional diagram of the photodiode-type battery-free gas sensor according to one example embodiment of the present inventive concept.

FIG. 1 is a schematic diagram illustrating a structure of the photodiode-type battery-free gas sensor according to one example embodiment of the present inventive concept, and FIG. 2 is a cross-sectional diagram of the photodiode-type battery-free gas sensor according to one example embodiment of the present inventive concept.

Referring to FIGS. 1 and 2, the photodiode-type battery-free gas sensor according to the present inventive concept includes a semiconductor substrate 10, insulator layers 20a and 20b, photoelectron collection electrodes 30, a semiconductor oxide layer 40, metal nanoparticle catalysts 50, an upper electrode 60, a lower electrode 70, and a metal-organic framework layer 80.

The semiconductor substrate 10 may be a semiconductor substrate made of a semiconductor. Examples of the semiconductor forming the semiconductor substrate may include silicon, gallium arsenide, gallium nitride, zinc oxide, indium phosphorus, silicon carbide, or the like and preferably may include p-type silicon. The substrate is formed to have any shape and typically have a flat plate shape.

The insulator layers 20a and 20b serve to prevent a short circuit between the electrodes and the substrate and include a first insulator layer 20a for forming the upper electrode layer and a second insulator layer 20b for forming the photoelectron collection electrodes layer. In this case, the first insulator layer 20a may be formed on a part of the substrate. The second insulator layer 20b is partially in contact with the first insulator layer 20a, and a length direction of the second insulator layer 20b is perpendicular to a length direction of the first insulator layer. The second insulator layer 20b forms linear patterns at certain intervals. The linear patterns of the second insulator layer 20b are for forming linear patterns of the photoelectron collection electrodes.

The insulator layers 20a and 20b may be made of silicon oxide ($SiO_2$) or aluminum oxide ($Al_2O_3$), but the present inventive concept is not limited thereto.

The insulator layers 20a and 20b are preferably formed to have a thickness of 50 nm or more. When the thickness of the insulator layers is less than 50 nm, the insulator layers may not successfully serve to prevent a short circuit. More preferably, the insulator layers 20a and 20b may have a thickness ranging from 50 nm to 200 nm. In the insulator layers 20a and 20b, the first insulator layer 20a and the second insulator layer 20b may have different thicknesses.

The photoelectron collection electrode 30 serves to receive photoelectrons generated in a P-N junction region by light incident thereon and transfer the photoelectrons to a circuit to form a photocurrent. The photoelectron collection electrode 30 is formed on the second insulator layer. As shown in FIGS. 1 and 2, a stacked structure of the photoelectron collection electrodes 30 and the second insulator layer 20b forms linear patterns spaced apart from each other by a certain interval. In this case, the interval between the patterns of the photoelectron collection electrodes 30 is preferably in a range of 5 μm to 30 μm. Then, a semiconductor oxide layer is deposited to form a P-N junction between the photoelectron collection electrodes 30, and gas adsorption occurs on a surface of the semiconductor oxide layer. When the interval between the patterns of the photoelectron collection electrodes 30 is less than 5 μm, an adsorption area with respect to a gas is too small, and thus, it is difficult to detect the gas. When the interval exceeds 30 μm, a distance to the photoelectron collection electrode is too long, and thus, it is difficult to collect photoelectrons. Accordingly, a photocurrent may not flow. The photoelectron collection electrode 30 may be formed on the first insulator layer 20a and the second insulator layer 20b and may be formed to have a thickness ranging from 20 nm to 40 nm, but the present inventive concept is not limited thereto.

A material of the photoelectron collection electrode may be selected from the group consisting of, for example, platinum (Pt), aluminum (Al), gold (Au), copper (Cu), tungsten (W), titanium (Ti), and chromium (Cr), but the present inventive concept is not limited thereto.

The semiconductor oxide layer 40 is bonded to the semiconductor substrate to form a P-N junction and thus generate photoelectrons from incident light. In addition, the semiconductor oxide layer 40 serves to adsorb a target gas together with the metal nanoparticle catalysts.

In this case, when the semiconductor substrate is made of a p-type semiconductor material, the semiconductor oxide layer may be made of an n-type semiconductor material, and when the semiconductor substrate is made of an n-type semiconductor material, the semiconductor oxide layer may be made of a p-type semiconductor material.

The p-type semiconductor material can be applied to a substrate and may be for example, p-type silicon or indium gallium nitride, and the n-type semiconductor material can be applied as a semiconductor oxide and may be selected from the group consisting of, for example, indium gallium zinc oxide (IGZO), zinc oxide (ZnO), tin dioxide ($SnO_2$), and titanium dioxide ($TiO_2$), but the present inventive concept is not limited thereto.

As shown in FIGS. 1 and 2, the semiconductor oxide layer 40 may be formed to cover a portion of the semiconductor substrate 10 adjacent thereto and a portion or an entirety of the photoelectron collection electrode 30 comprising the second insulator layer 20b on the semiconductor substrate 10.

A thickness of the semiconductor oxide layer 40 may be adjustable. For example, the semiconductor oxide layer 40 may be formed to have a thickness ranging from 20 nm to 40 nm, but the present inventive concept is not limited thereto.

The incident light may be visible light or light-emitting diode (LED) light but is not limited thereto.

The metal nanoparticle catalysts 50 are formed on the semiconductor oxide layer 40 and are introduced to induce smooth adsorption or desorption of a target gas. A type of the metal nanoparticle catalyst 50 may be appropriately selected according to the target gas. For example, when the target gas is a hydrogen gas, a palladium (Pd) catalyst may be used as the metal nanoparticle catalyst, when the target gas is an $NO_2$ gas, a nickel (Ni) catalyst may be used as the metal nanoparticle catalyst, and when the target gas is an $H_2S$ gas, a copper (Cu) catalyst may be used as the metal nanoparticle catalyst.

The upper electrode 60 and the lower electrode 70 are for forming a circuit to measure a photocurrent. The upper electrode 60 may be formed to cover portions of the photoelectron collection electrodes formed on the first insulator layer so as to be connected to the photoelectron collection electrodes, and the lower electrode 70 may be formed below the substrate.

The upper electrode 60 and the lower electrode 70 may be made of a commonly used electrode material, for example, at least one selected from the group consisting of Pt, Al, Au, Cu, W, Ti, and Cr, but the present inventive concept is not limited thereto. A thickness of the upper electrode 60 and the lower electrode 70 may be adjustable. For example, the upper electrode 60 and the lower electrode 70 may be formed to have a thickness ranging from 20 nm to 40 nm, but the present inventive concept is not limited thereto.

A metal-organic framework MOF constituting the metal-organic framework layer 80 may be made of a crystalline compound, which is formed by bonding metal ions with organic ligand, and may have a one-, two-, or three-dimensional structure and contain a large amount of micro pores therein. The present inventive concept includes the metal-organic framework layer 80, and the metal-organic framework layer 80 serves to prevent aggregation and surface pollution of the metal nanoparticle catalysts and to induce gas aggregation, thereby improving gas detection performance A metal of the metal-organic framework is not particularly limited and may be selected from the group consisting of iron, aluminum, zinc, chromium, zirconium, and copper.

A specific surface area of the metal-organic framework is not particularly limited and may preferably be in a range of 100 $m^2/g$ to 4,300 $m^2/g$ and more preferably in a range of 200 $m^2/g$ to 2,500 $m^2/g$. This is because, when the specific surface area is less than 100 $m^2/g$, although the metal-organic framework is composited, the metal-organic framework has very low adsorption and permeation performance as a porous support, and a metal-organic framework with a surface area exceeding 4,300 m$^2$/g is not currently produced.

A density of the metal-organic framework is not particularly limited but may preferably be in a range of 0.1 g/cm$^3$ to 1.0 g/cm$^3$ and more preferably in a range of 0.1 g/cm$^3$ to 0.6 g/cm$^3$. This is because a metal-organic framework with a density less than 0.1 g/cm$^3$ is not produced, and a metal-organic framework with a density exceeding 1.0 g/cm$^3$ does not have a sufficient specific surface area and thus has low adsorption efficiency with respect to a target molecule.

For example, the metal-organic framework used in the present inventive concept may include at least one selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate), but the present inventive concept is not particularly limited thereto.

A thickness of the metal-organic framework layer 80 may be adjustable. For example, the metal-organic framework layer 80 may be formed to have a thickness ranging from 20 nm to 40 nm, but the present inventive concept is not limited thereto.

Method of Manufacturing Photodiode-Type Battery-Free Gas Sensor

Figure 3:
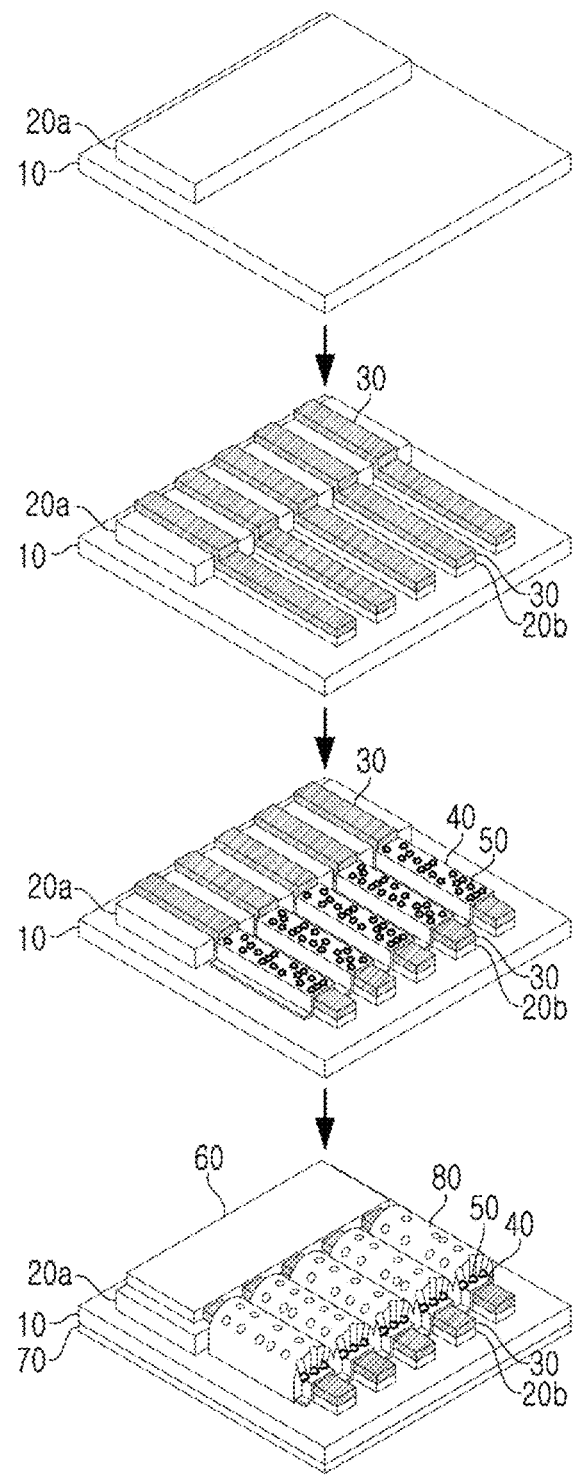
FIG. 3 shows schematic diagrams illustrating a method of manufacturing a photodiode-type battery-free gas sensor according to one example embodiment of the present inventive concept.

FIG. 3 shows schematic diagrams illustrating a method of manufacturing a photodiode-type battery-free gas sensor according to one example embodiment of the present inventive concept.

Referring to FIG. 3, the method of manufacturing the photodiode-type battery-free gas sensor according to the present inventive concept includes a) forming a first insulator layer 20a for an upper electrode on a part of an upper portion of a semiconductor substrate 10, b) forming a stacked structure of photoelectron collection electrodes 30 and a second insulator layer 20b, which are formed with linear patterns spaced apart from each other by a certain interval, on the upper portion of the semiconductor substrate comprising the first insulator layer 20a, c) forming a semiconductor oxide layer 40 which covers the stacked structure of the photoelectron collection electrodes 30 and the second insulator layer 20b, d) forming metal nanoparticle catalysts 50 on the semiconductor oxide layer 40, e) forming a metal-organic framework layer 80 which covers the semiconductor oxide layer 40 and the metal nanoparticle catalysts 50, f) forming an upper electrode 60 which covers the photoelectron collection electrodes 30 formed on the first insulator layer 20a, and g) forming a lower electrode 70 below the semiconductor substrate 10.

Hereinafter, the method of manufacturing the photodiode-type battery-free gas sensor of the present inventive concept will be described in detail for each operation.

First, operation a) is an operation of forming the first insulator layer 20a for an upper electrode on the upper portion of the semiconductor substrate 10.

Examples of a semiconductor forming the semiconductor substrate may include silicon, gallium arsenide, gallium nitride, zinc oxide, indium phosphorus, silicon carbide, or the like and preferably may include p-type silicon. The substrate is formed to have any shape and typically have a flat plate shape. The semiconductor substrate may be preprocessed through ultrasonic cleaning or the like to remove impurities.

The first insulator layer 20a may be formed on a part of the upper portion of the semiconductor substrate. In this case, the first insulator layer 20a may be formed using a method of forming the first insulator layer 20a only in a specific region of the substrate or a method of forming the first insulator layer 20a in an entire region of the substrate and then leaving only a specific region of the substrate and removing the remaining region of the substrate using an etchant.

Here, the first insulator layer 20a may be formed using at least one method selected from an e-beam evaporation method, a thermal evaporation method, an atomic layer deposition method, a sputtering method, silicon dry oxidation, and silicon wet oxidation, but the present inventive concept is not limited thereto.

The first insulator layer 20a may preferably be made of silicon oxide ($SiO_2$) or aluminum oxide ($Al_2O_3$), but the present inventive concept is not limited thereto.

The first insulator layer 20a is preferably formed to have a thickness of 50 nm or more. When the thickness of the first insulator layer is less than 50 nm, the first insulator layer may not successfully serve to prevent a short circuit. More preferably, the first insulator layer may have a thickness ranging from 50 nm to 200 nm.

Next, operation b) is an operation of forming the stacked structure of the photoelectron collection electrodes 30 and the second insulator layer 20b, which has the form of the linear patterns, on the upper portion of the semiconductor substrate 10.

In the stacked structure of the photoelectron collection electrodes 30 and the second insulator layer 20b, the linear patterns spaced apart from each other by a certain interval may be formed by performing a photolithography process. Since the photolithography process is a method commonly used in the art, detailed descriptions thereof will be omitted. In one example embodiment of the present inventive concept, after a linear pattern frame was formed using a photoresist, a frame of the photoresist was disposed on a substrate, the second insulator layer and a layer of the photoelectron collection electrodes were sequentially deposited, and then, the photoresist was removed. Such a deposition method may use an e-beam evaporation method, a sputtering method, or the like, but the present inventive concept is not limited thereto.

In this case, an interval between the linear patterns is preferably in a range of 5 μm to 30 μm. When the interval between the linear patterns is less than 5 μm, an adsorption area with respect to a gas is too small, and thus it is difficult to detect the gas. When the interval exceeds 30 μm, a distance to the photoelectron collection electrode is too long, and thus, it is difficult to collect photoelectrons. Accordingly, a photocurrent may not flow The second insulator layer 20b may preferably be made of silicon oxide ($SiO_2$) or aluminum oxide ($Al_2O_3$), but the present inventive concept is not limited thereto.

The second insulator layer 20b is preferably formed to have a thickness of 50 nm or more. When the thickness of the second insulator layer is less than 50 nm, the second insulator layer may not successfully serve to prevent a short circuit. More preferably, the second insulator layer may have a thickness ranging from 50 nm to 200 nm. The first insulator layer 20a and the second insulator layer 20b may have different thicknesses.

A material of the photoelectron collection electrode may be selected from the group consisting of, for example, Pt, Al, Au, Cu, W, Ti, and Cr, but the present inventive concept is not limited thereto. A thickness of the photoelectron collection electrode may be adjustable. For example, the photoelectron collection electrode may be formed to have a thickness ranging from 20 nm to 40 nm, but the present inventive concept is not limited thereto.

Thereafter, the photoresist may be removed using an organic solvent such as acetone.

Next, operation c) is an operation of forming the semiconductor oxide layer 40.

The semiconductor oxide layer 40 is a layer which forms a P-N junction with the semiconductor substrate. When the semiconductor substrate is made of a p-type semiconductor material, the semiconductor oxide layer may be made of an n-type semiconductor material, and when the semiconductor substrate is made of an n-type semiconductor material, the semiconductor oxide layer may be made of a p-type semiconductor material.

The p-type semiconductor material can be applied to a substrate and may include, for example, p-type silicon or indium gallium nitride, and the n-type semiconductor material can be applied as a semiconductor oxide and may be selected from the group consisting of, for example, indium gallium zinc oxide (IGZO), zinc oxide (ZnO), tin dioxide ($SnO_2$), and titanium dioxide ($TiO_2$), but the present inventive concept is not limited thereto.

The semiconductor oxide layer 40 may be deposited through a method commonly used in the art. For example, a radio frequency (RF) sputtering method or the like may be used, but the present inventive concept is not limited thereto. The semiconductor oxide layer 40 may be formed to cover the stacked structure of the photoelectron collection electrodes 30 and the second insulator layer 20b on the semiconductor substrate 10.

A thickness of the semiconductor oxide layer 40 may be adjustable. For example, the semiconductor oxide layer 40 may be formed to have a thickness ranging from 20 nm to 40 nm, but the present inventive concept is not limited thereto.

After the semiconductor oxide layer 40 is deposited, a post-heat treatment process may be performed.

Next, operation d) is a process of forming the metal nanoparticle catalysts 50.

The metal nanoparticle catalyst 50 may be formed on the semiconductor oxide layer 40 to induce smooth adsorption or desorption of a target gas.

A type of the metal nanoparticle catalyst 50 may be appropriately selected according to the target gas. For example, when the target gas is a hydrogen gas, a Pd catalyst may be used as the metal nanoparticle catalyst, when the target gas is an $NO_2$ gas, a Ni catalyst may be used as the metal nanoparticle catalyst, and when the target gas is an $H_2S$ gas, a Cu catalyst may be used as the metal nanoparticle catalyst.

The metal nanoparticle catalyst 50 may be deposited through a method commonly used in the art. For example, an e-beam evaporation method or the like may be used, but the present inventive concept is not limited thereto.

Next, operation e) is an operation of forming the metal-organic framework layer 80.

The metal-organic framework layer 80 may be formed on the semiconductor oxide layer 40 to prevent aggregation and surface pollution of the metal nanoparticle catalyst 50 and improve gas detection performance by inducing a gas aggregation effect through nanopores formed in a surface thereof. In this case, the metal-organic framework layer 80 may be formed to cover the semiconductor oxide layer 40 and the metal nanoparticle catalyst 50.

A metal of a metal-organic framework constituting the metal-organic framework layer 180 is not particularly limited and may be selected from the group consisting of iron, aluminum, zinc, chromium, zirconium, and copper.

For example, the metal-organic framework may include, for example, at least one selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate), but the present inventive concept is not particularly limited thereto.

The metal-organic framework layer 80 may be formed through a method commonly used in the art. For example, an element on which deposition is performed up to operation d) may be dipped into a metal ion solution, and an organic material solution may be added and reacted therewith so that the element is coated with the metal-organic framework layer 80, but the present inventive concept is not limited thereto.

A thickness of the metal-organic framework layer 80 may be adjustable by repeating a coating operation. For example, the metal-organic framework layer 80 may be formed to have a thickness ranging from 200 nm to 400 nm, but the present inventive concept is not limited thereto.

Next, operation f) is an operation of forming the upper electrode 60.

The upper electrode 60 is formed to cover the photoelectron collection electrodes 30 formed on the first insulator layer 20a so as to be connected to the photoelectron collection electrodes. The upper electrode 60 may be deposited through a method commonly used in the art. For example, an e-beam deposition method, an RF sputtering method, or the like may be used, but the present inventive concept is not limited thereto.

The upper electrode 60 may be made of an electrode material commonly used in the art, for example, at least one selected from the group consisting of Pt, Al, Au, Cu, W, Ti, and Cr, but the present inventive concept is not limited thereto. A thickness of the upper electrode 60 may be adjustable. For example, the upper electrode 60 may be formed to have a thickness ranging from 20 nm to 40 nm, but the present inventive concept is not limited thereto.

Next, operation g) is an operation of forming the lower electrode 70.

The lower electrode 70 may be formed below the substrate and may be deposited through a method commonly used in the art. For example, an e-beam deposition method, an RF sputtering method, or the like may be used, but the present inventive concept is not limited thereto.

The lower electrode 70 may be made of an electrode material commonly used in the art, for example, at least one selected from the group consisting of Pt, Al, Au, Cu, W, Ti, and Cr, but the present inventive concept is not limited thereto. A thickness of the lower electrode 70 may be adjustable. For example, the upper electrode 60 may be formed to have a thickness ranging from 20 nm to 40 nm, but the present inventive concept is not limited thereto.

Method of Operating Photodiode-Type Battery-Free Gas Sensor

Hereinafter, a method of operating a photodiode-type battery-free gas sensor according to the present inventive concept will be described.

Figure 4:
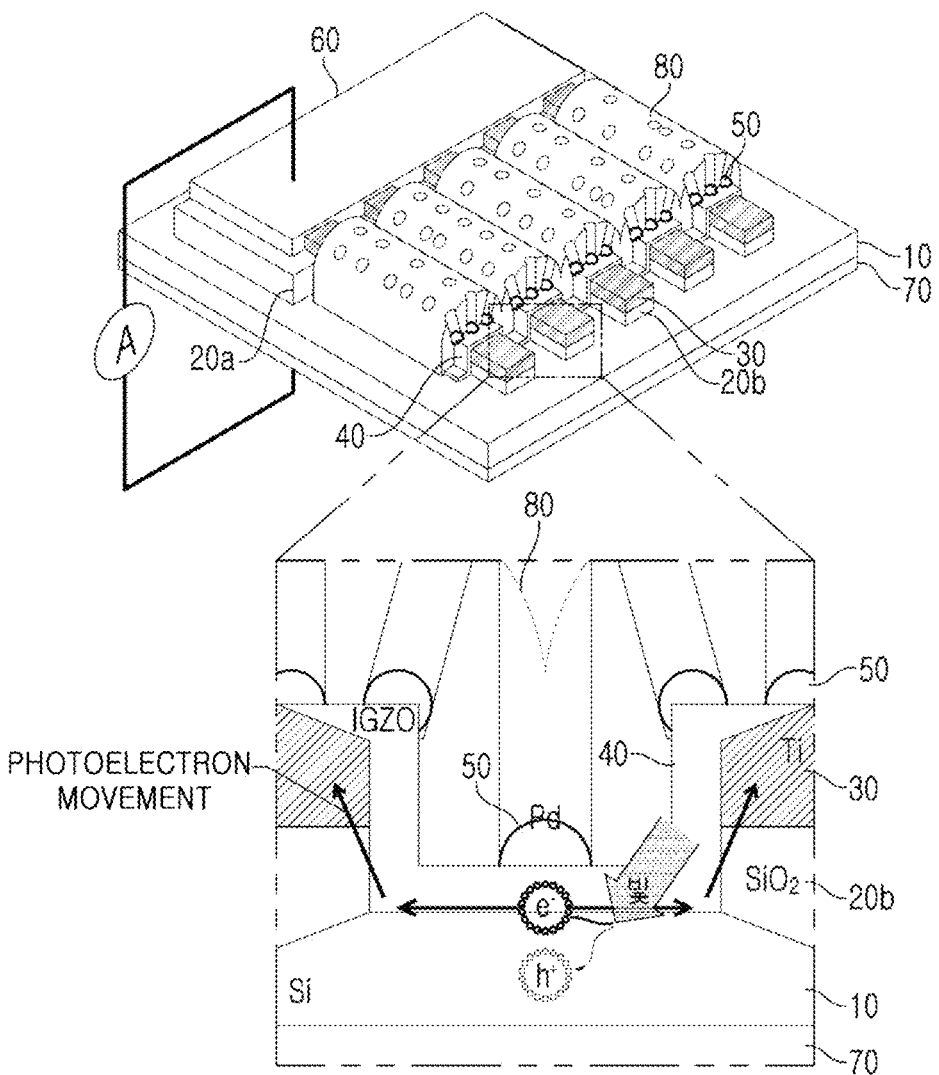
FIG. 4 shows schematic diagrams illustrating an operating principle of a photodiode-type battery-free gas sensor according to one example embodiment of the present inventive concept.
Figure 5:
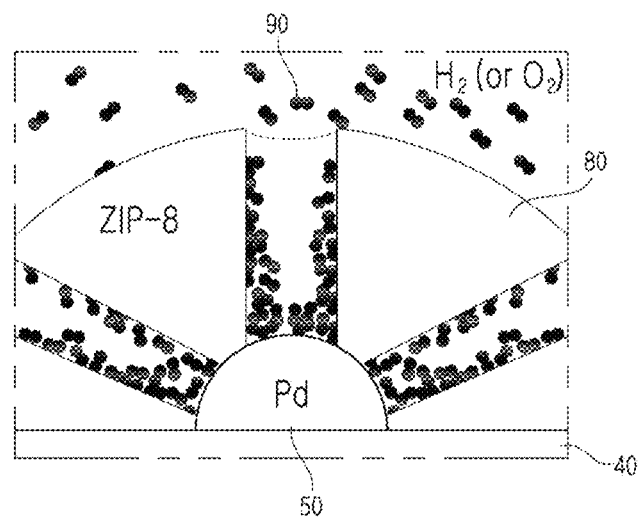
FIG. 5 is a schematic diagram illustrating an operating principle of a metal-organic framework in the photodiode-type battery-free gas sensor according to one example embodiment of the present inventive concept.

FIG. 4 shows schematic diagrams illustrating an operating principle of a photodiode-type battery-free gas sensor according to one example embodiment of the present inventive concept, and FIG. 5 is a schematic diagram illustrating an operating principle of a metal-organic framework.

As shown in FIG. 4, when light is incident on the photodiode-type battery-free gas sensor according to the present inventive concept, the incident light comes into contact with a P-N junction interface at which a substrate and a semiconductor oxide layer meet, and thus, photoelectrons are generated at the P-N junction interface. The generated photoelectrons are moved to the photoelectron collection electrode, and holes are collected in the bottom electrode past the Si substrate, and thus, a photocurrent flows.

In this case, a collection rate of the photoelectrons is determined by conductivity of the semiconductor oxide layer. When a target gas is absorbed into the semiconductor oxide layer due to the catalyst action of metal nanoparticles formed on the semiconductor oxide layer, the conductivity of the semiconductor oxide layer is changed. Thus, an amount of the photoelectrons collected in the photoelectron collection electrodes is reversibly changed, whereby a value of the photocurrent is also changed. The presence or absence of the target gas may be detected by detecting a change in the photocurrent.

In this case, as shown in FIG. 5, the target gas, which is collected by the semiconductor oxide layer and nanopores of a metal-organic framework formed on the metal nanoparticles, aggregates, and thus, a concentration of the target gas reacting with the metal nanoparticles is increased. Accordingly, detection sensitivity is improved.

As described above, unlike a general system in which a sensor and an element are driven using a solar cell, in the photodiode-type battery-free gas sensor according to the present inventive concept, a photodiode itself may serve as a gas sensor, and thus, there is no need for additional elements for generating, storing, and transmitting energy. Therefore, since the photodiode-type battery-free gas sensor does not include a high-capacity storage device such as a battery, the photodiode-type battery-free gas sensor may be manufactured in a very small size and may be applied in various ways, such as being attached to a portable device such as a smartphone or a smartwatch.

Photodiode-Type Battery-Free Humidity Sensor

Meanwhile, the present inventive concept provides a photodiode-type battery-free humidity sensor.

Hereinafter, a photodiode-type battery-free humidity sensor according to one example embodiment of the present inventive concept will be described in detail with reference to FIGS. 9 and 10.

Figure 9:
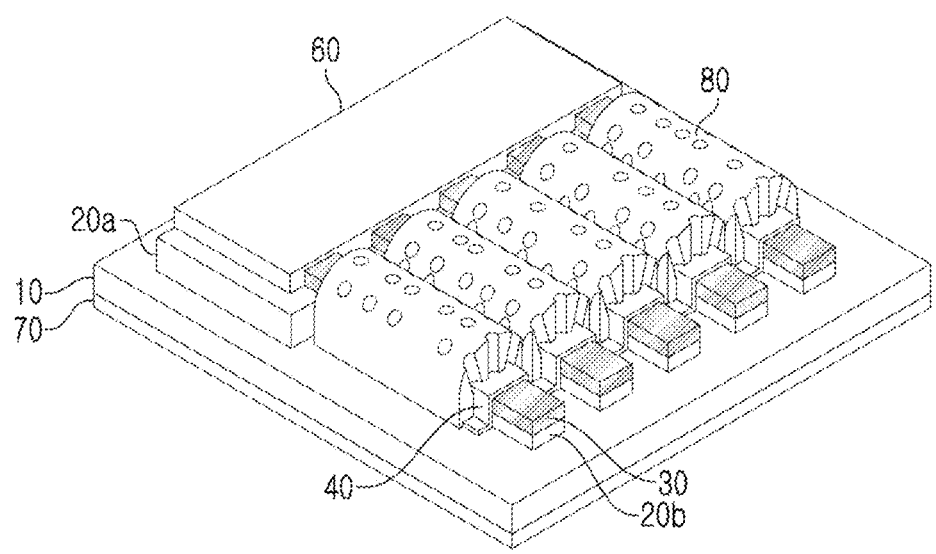
FIG. 9 is a schematic diagram of a photodiode-type battery-free humidity sensor according to another example embodiment of the present inventive concept.
Figure 10:
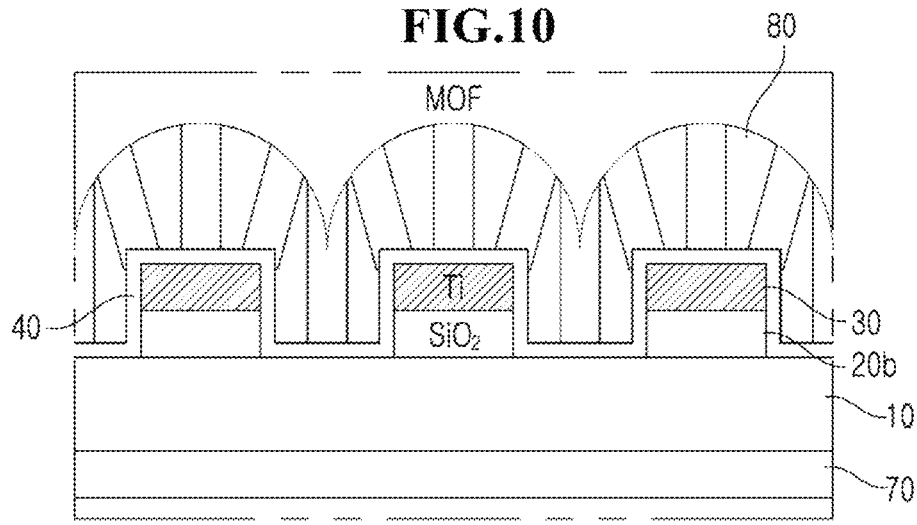
FIG. 10 is a cross-sectional diagram of the photodiode-type battery-free humidity sensor according to another example embodiment of the present inventive concept.

FIG. 9 is a schematic diagram of the photodiode-type battery-free humidity sensor according to another example embodiment of the present inventive concept, and FIG. 10 is a cross-sectional diagram of the photodiode-type battery-free humidity sensor according to another example embodiment of the present inventive concept.

The photodiode-type battery-free humidity sensor according to the present inventive concept has a configuration in which metal nanoparticle catalysts 50 are omitted from the above-described photodiode-type battery-free gas sensor. Referring to FIGS. 9 and 10, the photodiode-type battery-free humidity sensor includes a semiconductor substrate 10, insulator layers 20a and 20b, photoelectron collection electrodes 30, a semiconductor oxide layer 40, an upper electrode 60, a lower electrode 70, and a metal-organic framework layer 80.

Since the semiconductor substrate 10, the insulator layers 20a and 20b, the photoelectron collection electrodes 30, the semiconductor oxide layer 40, the upper electrode 60, the lower electrode 70, and the metal-organic framework layer 80 are the same as those of the above-described photodiode-type battery-free gas sensor, detailed descriptions thereof are omitted to avoid redundant descriptions.

Method of Manufacturing Photodiode-Type Battery-Free Humidity Sensor

Hereinafter, a method of manufacturing a photodiode-type battery-free humidity sensor according to the present inventive concept will be described.

Figure 11:
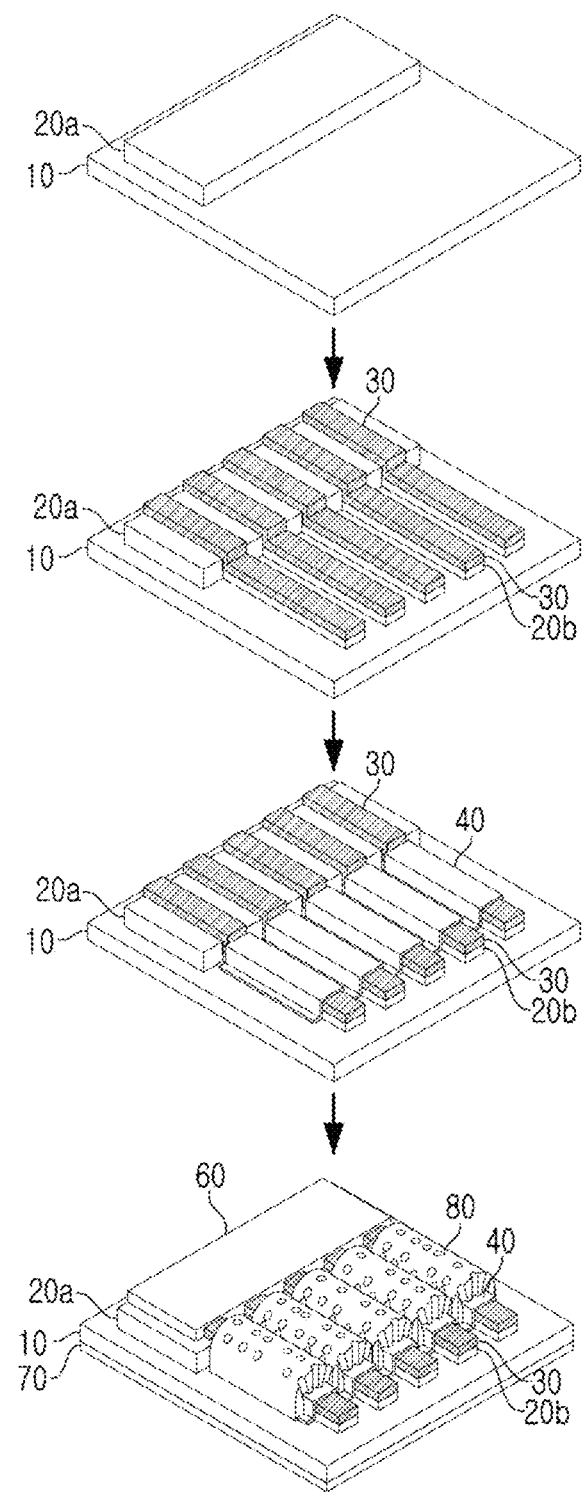
FIG. 11 is a schematic diagram illustrating a method of manufacturing a photodiode-type battery-free humidity sensor according to another example embodiment of the present inventive concept.

FIG. 11 is a schematic diagram illustrating the method of manufacturing the photodiode-type battery-free humidity sensor according to another example embodiment of the present inventive concept.

Referring to FIG. 11, the method of manufacturing the photodiode-type battery-free humidity sensor according to the present inventive concept includes a) forming a first insulator layer 20a for an upper electrode on a part of an upper portion of a semiconductor substrate 10, b) forming a stacked structure of photoelectron collection electrodes 30 and a second insulator layer 20b, which are formed with linear patterns spaced apart from each other by a certain interval, on the upper portion of the semiconductor substrate comprising the first insulator layer 20a, c) forming a semiconductor oxide layer 40 which covers the stacked structure of the photoelectron collection electrodes 30 and the second insulator layer 20b, d) forming a metal-organic framework layer 80 which covers the semiconductor oxide layer 40, e) forming an upper electrode 60 which covers the photoelectron collection electrodes 30 formed on the first insulator layer 20a, and f) forming a lower electrode 70 below the semiconductor substrate 10.

In the present inventive concept, since the method of manufacturing the humidity sensor is the same as the above-described method of manufacturing the photodiode-type battery-free gas sensor, except for an operation of forming the metal nanoparticle catalyst, detailed descriptions of each operation are omitted to avoid redundant descriptions.

Method of Operating Photodiode-Type Battery-Free Humidity Sensor

Hereinafter, a method of operating a photodiode-type battery-free humidity sensor according to the present inventive concept will be described Like the above-described method of operating the photodiode-type battery-free gas sensor, when light is incident on the photodiode-type battery-free humidity sensor according to the present inventive concept, the incident light is absorbed to a P-N junction interface at which a substrate and a semiconductor oxide layer meet, and thus, photoelectrons are generated at the P-N junction interface. The generated photoelectrons are moved to the photoelectron collection electrode, and holes are collected in the bottom electrode past the Si substrate, and thus, a photocurrent flows. In this case, a collection rate of the photoelectrons is determined by conductivity of the semiconductor oxide layer. When moisture adsorbed in nanopores of a metal-organic framework layer formed on the semiconductor oxide layer comes into contact with the semiconductor oxide layer, the conductivity of the semiconductor oxide layer is changed. Thus, an amount of the photoelectrons collected in the photoelectron collection electrodes is reversibly changed, whereby a value of the photocurrent is also changed. Humidity may be detected by detecting a change in the photocurrent.

Photodiode-Type Battery-Free Gas Sensor System

In addition, the present inventive concept provides a photodiode-type battery-free gas sensor system.

In general, a gas sensor should always have a constant sensibility with respect to a certain concentration of a gas. However, when surrounding environmental variables of the gas sensor, for example, humidity and the like are changed, an output signal of the sensor obtained by measuring a certain concentration of a gas is not constant and is changed due to such environmental change factors. Therefore, when the output signal with respect to the concentration of the gas is not properly corrected, incorrect determination may be caused and cause a big problem.

Figure 14:
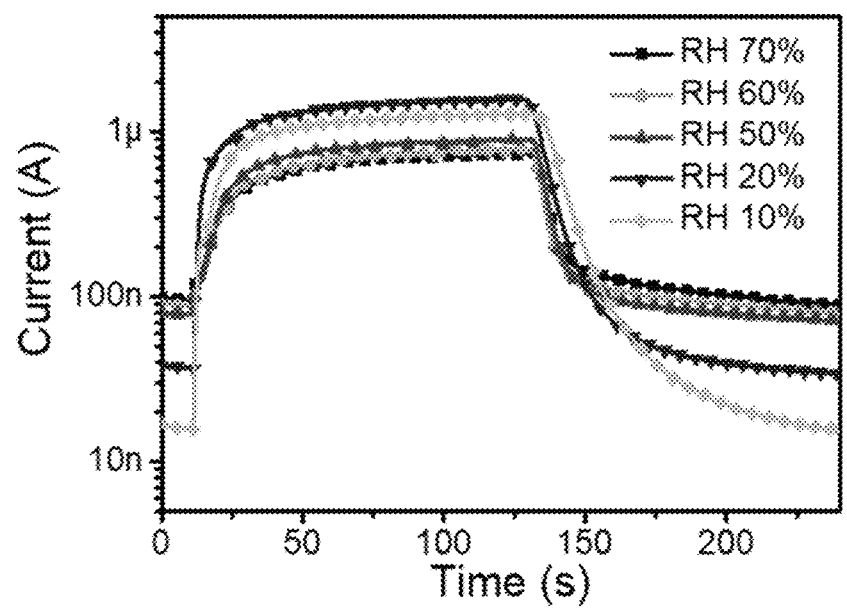
FIG. 14 is a graph showing humidity detection performance according to the presence and absence of a metal-organic framework layer in a photodiode-type battery-free humidity sensor according to another example embodiment of the present inventive concept.

As shown in FIG. 14, even in a photodiode-type battery-free gas sensor according to the present inventive concept, as humidity is changed, an amount of a photocurrent is changed before and after exposure to hydrogen, and thus, it is confirmed that sensitivity is changed according to humidity.

Therefore, correction technology capable of controlling such an influence of humidity on a sensor should be secured.

When the photodiode-type battery-free gas sensor and the photodiode-type battery-free humidity sensor according to the present inventive concept are used together, the sensitivity of the gas sensor may be corrected in real time based on measurement results of the humidity sensor, thereby accurately measuring a concentration of a target gas regardless of humidity.

Accordingly, the present inventive concept provides a photodiode-type battery-free gas sensor system comprising both of a photodiode-type battery-free gas sensor and a photodiode-type battery-free humidity sensor.

Figure 16:
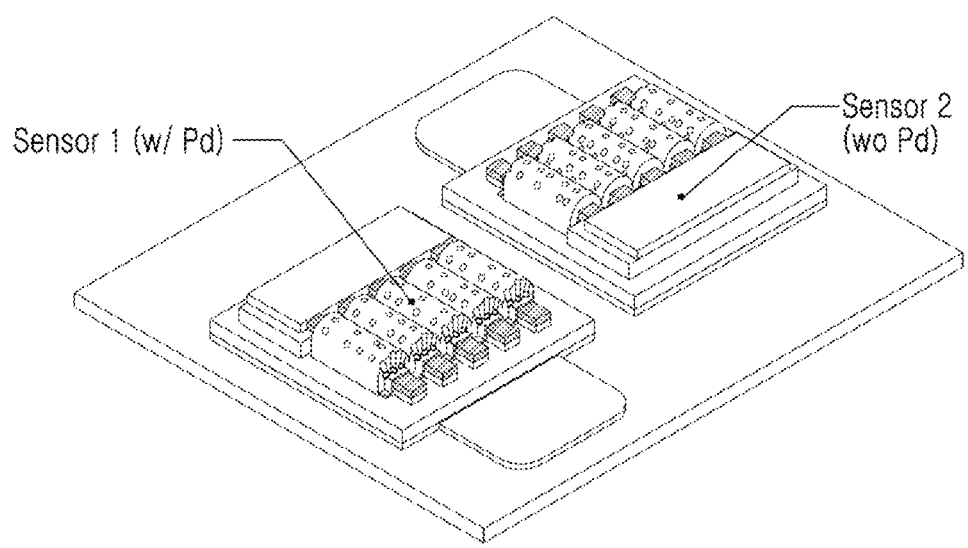
FIG. 16 is a schematic diagram of a photodiode-type battery-free gas sensor system, in which humidity correction is performed, comprising both of a photodiode-type battery-free humidity sensor and a photodiode-type battery-free gas sensor according to still another example embodiment of the present inventive concept.

As shown in FIG. 16, the photodiode-type battery-free gas sensor system may include the photodiode-type battery-free gas sensor and the photodiode-type battery-free humidity sensor and may further include an output signal correction module which calculates a target gas concentration using a gas sensor output signal acquired from the gas sensor and humidity data acquired from the humidity sensor, a concentration detection module which calculates a target gas concentration from an output signal corrected based on an output signal reference model, a display module which displays concentration information, and a communication module which transmits measured concentration information to a main computer or a server.

Since the photodiode-type battery-free gas sensor and the photodiode-type battery-free humidity sensor are the same as those described above, detailed descriptions thereof are omitted to avoid redundant descriptions.

Unlike a general system in which a sensor and an element are driven using a solar cell, in the photodiode-type battery-free gas sensor or humidity sensor according to the present inventive concept, a photodiode itself may serve as a gas sensor, and thus, there is no need for additional elements for generating, storing, and transmitting energy. Therefore, since the photodiode-type battery-free gas sensor or humidity sensor does not include a high-capacity storage device such as a battery, the photodiode-type battery-free gas sensor or humidity sensor may be manufactured in a very small size and may be applied in various ways, such as being attached to a portable device such as a smartphone or a smartwatch.

In addition, in the photodiode-type battery-free gas sensor according to the present inventive concept, a porous metal-organic framework layer may be formed on metal nanoparticle catalysts to prevent aggregation and surface pollution of the metal nanoparticle catalysts, thereby improving stability. In addition, a target gas may aggregate to show an effect of improving sensitivity by eight times or more as compared with when there is no metal-organic framework layer. When the catalysts are not attached to the photodiode-type battery-free gas sensor, moisture may be adsorbed in micropores of a metallic-organic framework, and the photodiode-type battery-free gas sensor may be used as a humidity sensor. As a result, when the photodiode-type battery-free gas sensor and the photodiode-type battery-free humidity sensor are used together, humidity correction may be performed to accurately measure an amount of a gas.

Hereinafter, Manufacturing Examples and Experimental Examples are provided to help the understanding of the present inventive concept. However, the following Manufacturing Examples and Experimental Examples are merely provided to more easily understand the present inventive concept, and the present inventive concept is not limited to the following Manufacturing Examples and Experimental Examples.

<Manufacturing Example 1> Manufacture of Photodiode-Type Battery-Free Gas Sensor As shown in FIG. 3, a photodiode-type battery-free gas sensor was manufactured through the following method.

First, a 1.5 cm×1.5 cm sized p-type Si wafer (substrate) (with 1 to 10 Ωcm and SSP prime) was successively ultrasonically cleaned in acetone (95.5%, Duksan) and isopropyl alcohol (95.5%, Duksan) cleaning solution.

Next, a 100 nm $SiO_2$ layer (film) was deposited as a first insulator layer on the substrate using an electron beam evaporator (KVE-EG, Korea Vacuum Tech.). Subsequently, excluding a quarter of an upper portion of the $SiO_2$ film, the rest of the $SiO_2$ film was removed with a buffered oxide etchant (BOE) (J. T. Baker).

Then, after a photoresist was coated on the substrate and a rod-shaped linear pattern frame was formed by performing an exposure process using a photomask, a 50 nm $SiO_2$ layer as a second insulator layer was deposited within the linear pattern frame using e-beam deposition, and a 30 nm Ti layer as photoelectron collection electrodes was deposited on the second insulator layer using e-beam evaporation, thereby manufacturing electrodes with linear patterns spaced apart from each other by an interval of 20 μm. Thereafter, the photoresist was removed in acetone.

Next, an IGZO film (layer) was deposited to have a thickness of 30 nm to cover the Ti electrodes and the substrate adjacent to the Ti electrodes in a gas mixture of Ar and $O_2$ (Ar:$O_2$=100:2) at a static pressure of 10 mTorr by using an RF magnetron sputtering system (KVS-2003L, Korea Vacuum Tech.). An IGZO target included $In_2O_3$, $Ga_2O_3$, and ZnO at an atomic ratio of 1:1:1. After the IGZO film was deposited, a post-heat treatment process was performed at a temperature of 300° C. for 1 hour in an inert gas ($N_2$) environment.

Then, a Pd catalyst layer was deposited on the IGZO layer to have a thickness of 0.5 nm using an electron beam evaporator.

Next, such an element was introduced into alcohol in which $Zn^{2+}$ ions are dissolved at a concentration of 25 mM, and a 2-methylimidazole solution having the same concentration as $Zn^{2+}$ was added to apply a ZIF-8 layer. Such a coating operation was repeated twice to apply the ZIF-8 layer having a thickness of 300 nm.

After that, a gold electrode as an upper electrode was deposited though RF sputtering such that patterned electrodes positioned on the first insulator layer, i.e., the $SiO_2$ layer, were connected. Next, aluminum (Al) was deposited through RF sputtering below the Si substrate to form a lower electrode, thereby manufacturing a photodiode-type battery-free gas sensor.

<Manufacturing Example 2> Manufacture of Photodiode-Type Battery-Free Humidity Sensor As shown in FIG. 11, a photodiode-type battery-free humidity sensor was manufactured through the following method.

First, a 1.5 cm×1.5 cm sized p-type Si wafer (substrate) (with 1 to 10 Ωcm and SSP prime) was successively ultrasonically cleaned in acetone (95.5%, Duksan) and isopropyl alcohol (95.5%, Duksan) cleaning solution.

Next, a 100 nm $SiO_2$ layer (film) was deposited as a first insulator layer on the substrate using an electron beam evaporator (KVE-EG, Korea Vacuum Tech.). Subsequently, excluding a quarter of an upper portion of the $SiO_2$ film, the rest of the $SiO_2$ film was removed with a BOE (J. T. Baker).

Then, after a photoresist was coated on the substrate and a rod-shaped linear pattern frame was formed by performing an exposure process using a photomask, a 50 nm $SiO_2$ layer as a second insulator layer was deposited within the linear pattern frame using e-beam deposition, and a 30 nm Ti layer as photoelectron collection electrodes was deposited on the second insulator layer using e-beam evaporation, thereby manufacturing electrodes with linear patterns spaced apart from each other by an interval of 20 μm. Thereafter, the photoresist was removed in acetone.

Next, an IGZO film was deposited to have a thickness of 30 nm to cover the Ti electrodes and the substrate adjacent to the Ti electrodes in a gas mixture of Ar and $O_2$ (Ar: $O_2$=100:2) at a static pressure of 10 mTorr by using an RF magnetron sputtering system (KVS-2003L, Korea Vacuum Tech.). An IGZO target included $In_2O_3$, $Ga_2O_3$, and ZnO at an atomic ratio of 1:1:1. After the IGZO film was deposited, a post-heat treatment process was performed at a temperature of 300° C. for 1 hour in an inert gas ($N_2$) environment.

After that, such an element was introduced into alcohol in which $Zn^{2+}$ ions are dissolved at a concentration of 25 mM, and a 2-methylimidazole solution having the same concentration as $Zn^{2+}$ was added to apply a ZIF-8 layer. Such a coating operation was repeated twice to apply the ZIF-8 layer having a thickness of 300 nm.

Figure 12:
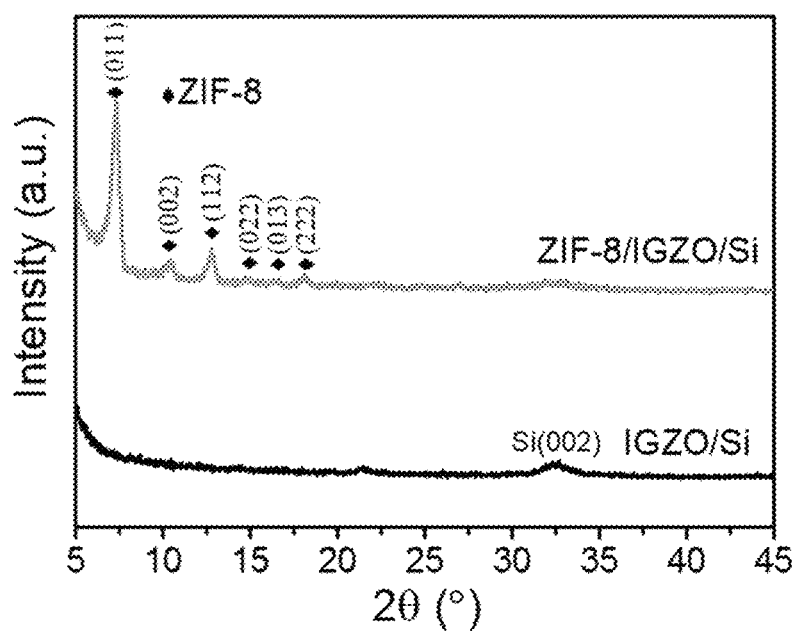
FIG. 12 is a graph showing an X-ray diffraction analysis (XRD) according to the presence and absence of a metal-organic framework layer in a photodiode-type battery-free humidity sensor according to one example embodiment of the present inventive concept.

An X-ray diffraction analysis (XRD) was performed on the formed ZIF-8 layer, and a result of the analysis was shown in FIG. 12.

FIG. 12 is a graph showing an XRD according to the presence and absence of a metal-organic framework layer in the photodiode-type battery-free humidity sensor according to one example embodiment of the present inventive concept.

As shown in FIG. 12, after the ZIF-8 layer, which is the metal-organic framework layer, was applied, XRD peaks corresponding to the ZIF-8 layer appeared in a 2θ range of 20° or less. Thus, it is confirmed that the ZIF-8 layer is successfully formed.

Next, the gold electrode as the upper electrode was deposited though RF sputtering such that the patterned electrodes positioned on the first insulator layer, i.e., the $SiO_2$ layer, were connected. Next, aluminum (Al) was deposited through RF sputtering below the Si substrate to form the lower electrode, thereby manufacturing the photodiode-type battery-free humidity sensor.

Figure 13:
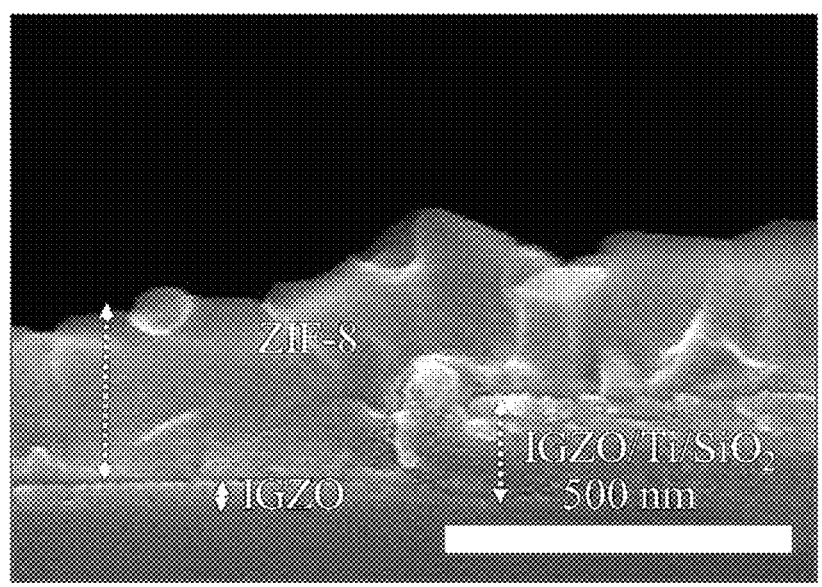
FIG. 13 is a scanning electron microscope image showing a cross section of electrodes with linear patterns in a photodiode-type battery-free humidity sensor comprising a metal-organic framework layer according to one example embodiment of the present inventive concept.

A cross section of the manufactured photodiode-type battery-free humidity sensor was observed with a scanning electron microscope and shown in FIG. 13.

FIG. 13 is a scanning electron microscope image showing a cross section of the electrodes of the linear patterns of the photodiode-type battery-free humidity sensor according to one example embodiment of the present inventive concept.

As shown in FIG. 13, as a result of observing a cross section of an electrode region of the linear patterns, it is confirmed that a junction region of p- and n-type semiconductors and a $Ti/SiO_2$ electrode region of a convex portion formed between the p- and n-type semiconductors are observed, and a metal-organic framework layer is formed on the junction region of the p- and n-type semiconductors and the $Ti/SiO_2$ electrode region.

<Comparative Example 1> Manufacture of Gas Sensor not Comprising Metal-Organic Framework Layer A photodiode-type battery-free gas sensor was manufactured in the same manner as in Manufacturing Example 1, except that an operation of forming a metal-organic framework layer was not performed.

<Comparative Example 2> Manufacture of Humidity Sensor not Comprising Metal-Organic Framework Layer A photodiode-type battery-free humidity sensor was manufactured in the same manner as in Manufacturing Example 2, except that an operation of forming a metal-organic framework layer was not performed.

<Experimental Example 1> Measurement of Hydrogen Gas Detection Performance of Photodiode-Type Battery-Free Gas Sensor According to the Presence and Absence of Metal-Organic Framework Layer In a photodiode-type battery-free gas sensor comprising a metal-organic framework layer according to the present inventive concept, in order to see an influence of an essential component, i.e., the organic metal-organic framework layer on gas detection performance, the following experiment was performed.

Specifically, in the photodiode-type battery-free gas sensors manufactured in Manufacturing Example 1 and Comparative Example 1, as shown in FIG. 4, a circuit, which connects an upper electrode and a lower electrode, was formed, and the photodiode-type battery-free gas sensor connected through the circuit was introduced into a handmade chamber provided with a mass flow controller (SEC-4550m, Horiba). While a concentration of a hydrogen gas was adjusted from 2% to 100 ppm, LED light corresponding to one-twentieth of the sunlight was irradiated onto the chamber to measure a photocurrent using a source meter in real time, thereby measuring gas detection performance of the sensor.

Figure 6:
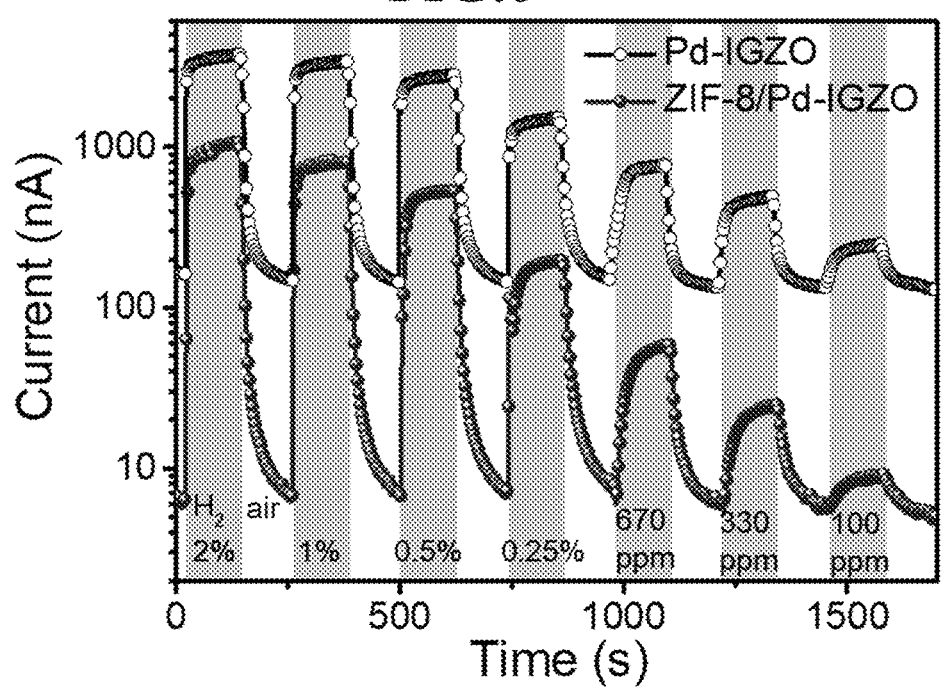
FIG. 6 is a graph showing hydrogen gas detection performance according to the presence and absence of a metal-organic framework layer in a photodiode-type battery-free gas sensor according to one example embodiment of the present inventive concept.

Results of the measurement were shown in FIG. 6.

FIG. 6 is a graph showing hydrogen gas detection performance of the photodiode-type battery-free gas sensor according to one Example of the present inventive concept or one Comparative Example.

As shown in FIG. 6, when hydrogen was supplied to a chamber accommodating the photodiode-type battery-free gas sensor according to the present inventive concept, an amount of a photocurrent was increased. Thus, it is confirmed that a hydrogen ($H_2$) gas at a concentration ranging from 100 ppm to 2% may be detected only by irradiating light without an additional power source.

In this case, the photodiode-type battery-free gas sensor according to the present inventive concept completed detection between 30 seconds to 60 seconds, and a minimum detection concentration thereof was 30 ppm.

In addition, as a result of comparing sensitivity of the gas sensors according to the presence and absence of the metal-organic framework layer, as shown in FIG. 6, the photodiode-type battery-free gas sensor comprising the metal-organic framework layer had high sensitivity, which was about eight times or more greater than that of the photodiode-type battery-free gas sensor not comprising the metal-organic framework layer.

Therefore, the photodiode-type battery-free gas sensor according to the present inventive concept may quickly detect a target gas within 60 seconds only by irradiating light without an additional power source, and a minimum detection concentration thereof may be 30 ppm. The photodiode-type battery-free gas sensor may be operated at the same sensitivity as a conventional high-sensitivity semiconductor-type gas sensor and may be manufactured in a very small size due to not requiring an external battery. In particular, since the photodiode-type battery-free gas sensor includes the metal-organic framework layer, sensitivity thereof may be increased by about eight times or more to detect a trace amount. Accordingly, the photodiode-type battery-free gas sensor may be usefully used for a variety of gas detection by using an appropriate nanoparticle catalyst.

<Experimental Example 2> Measurement of Multi-Time Usability of Photodiode-Type Battery-Free Gas Sensor Comprising Metal-Organic Framework Layer In order to measure a change in performance when a photodiode-type battery-free gas sensor comprising a metal-organic framework layer according to the present inventive concept was used multiple times, the photodiode-type battery-free gas sensor connected through a circuit was introduced into a handmade chamber provided with a mass flow controller (SEC-4550m, Horiba). While irradiating a LED light corresponding to one-twentieth of the sunlight consistently onto the chamber, and repeat injecting air and 0.5% hydrogen gas alternately for one minute each, a photocurrent of the sensor was measured with a source meter in real time.

Figure 7:
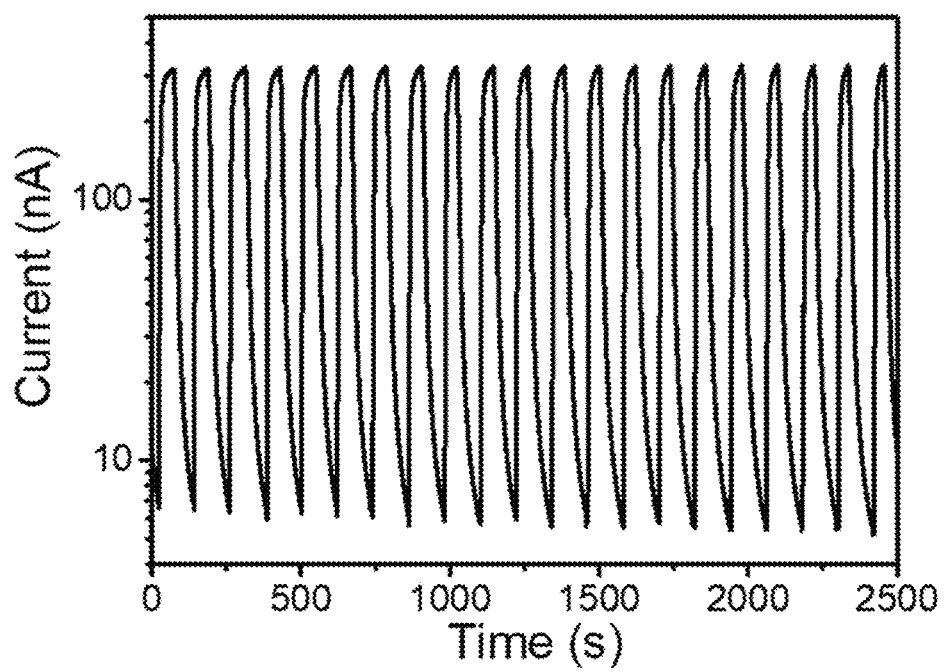
FIG. 7 is a graph showing hydrogen gas detection performance in multiple repeated measurements of photodiode-type battery-free gas sensor according to one example embodiment of the present inventive concept.

Results of the measurement were shown in FIG. 7.

As shown in FIG. 7, it can be seen that sensitivity remains the same even when the photodiode-type battery-free gas sensor comprising the metal-organic framework layer according to the present inventive concept is used multiple times.

<Experimental Example 3> Stability Experiment of Photodiode-Type Battery-Free Gas Sensor According to the Presence and Absence of Metal-Organic Framework Layer In a photodiode-type battery-free gas sensor comprising a metal-organic framework layer according to the present inventive concept, in order to see an influence of an essential component, i.e., the organic metal-organic framework layer on stability of the sensor, the following experiment was performed.

Specifically, in the photodiode-type battery-free gas sensors manufactured in Manufacturing Example 1 and Comparative Example 1, as shown in FIG. 4, a circuit, which connects an upper electrode and a lower electrode, was formed, and the photodiode-type battery-free gas sensor connected through the circuit was introduced into a handmade chamber provided with a mass flow controller (SEC-4550m, Horiba). While a concentration of a hydrogen gas was adjusted from 2% to 100 ppm, LED light corresponding to one-twentieth of the sunlight was irradiated onto the chamber to measure a photocurrent using a source meter in real time, thereby measuring gas detection performance of the sensor.

Figure 8B:
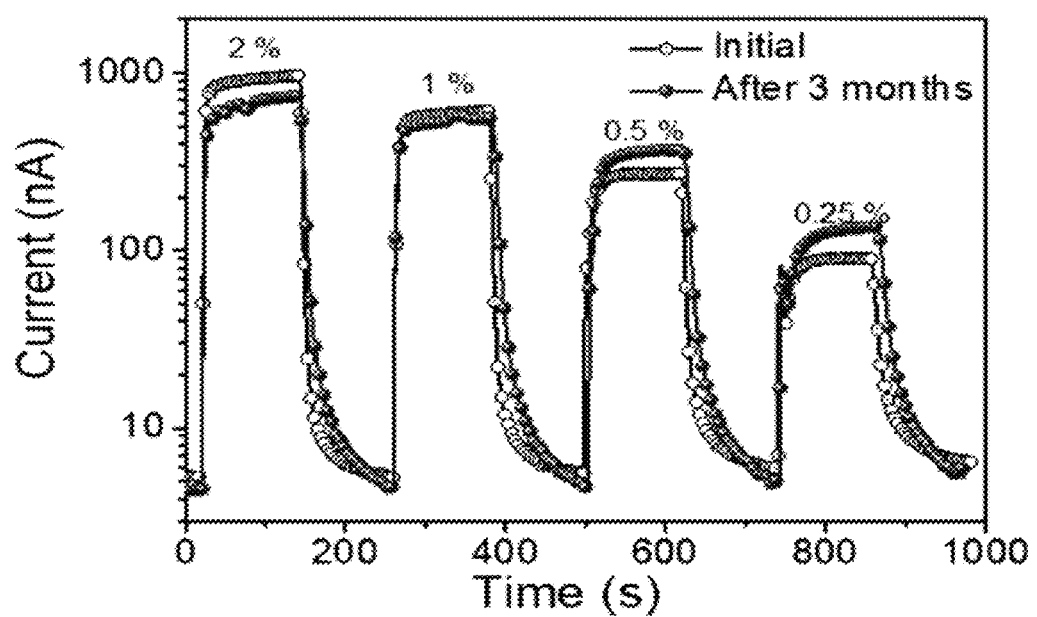
FIG. 8B is a graph showing hydrogen gas detection performance when a photodiode-type battery-free gas sensor according to one Example embodiment of the present inventive concept performs initial measurement and measurement after 3 months.

Next, after the sensors were stored in the air for 3 months, detection performance with respect to a hydrogen gas was measured again in real time in the same manner, and results of the measurement were shown in FIGS. 8A and 8B.

As shown in FIG. 8A, it is confirmed that in the photodiode-type battery-free gas sensor not comprising the metal-organic framework layer, after 3 months, sensitivity with respect to a gas is reduced, but in the photodiode-type battery-free gas sensor comprising the metal-organic framework layer according to the present inventive concept, even after 3 months, sensitivity with respect to a gas remains the same as in the initial measurement, as shown in FIG. 8B.

Therefore, since the photodiode-type battery-free gas sensor according to the present inventive concept includes the metal-organic framework layer, even after the photodiode-type battery-free gas sensor is stored for a long time, sensitivity thereof is not reduced but remains the same.

<Experimental Example 4> Evaluation of Influence of Humidity on Photodiode-Type Battery-Free Gas Sensor Comprising Metal-Organic Framework Layer In order to see an influence of humidity on a photodiode-type battery-free gas sensor comprising a metal-organic framework layer according to the present inventive concept, the following experiment was performed.

Specifically, in the photodiode-type battery-free gas sensor manufactured in Manufacturing Example 1, as shown in FIG. 4, a circuit, which connects an upper electrode and a lower electrode, was formed, and the photodiode-type battery-free gas sensor connected through the circuit was introduced into a handmade chamber provided with a mass flow controller (SEC-4550m, Horiba). While a concentration of moisture was adjusted from 10% to 70%, a hydrogen gas having a certain concentration was injected and LED light corresponding to one-twentieth of the sunlight was irradiated onto the chamber to measure a photocurrent using a source meter in real time, thereby measuring gas detection performance of the sensor. Results of the measurement were shown in FIG. 14.

As shown in FIG. 14, the photodiode-type battery-free gas sensor according to the present inventive concept exhibits sensitivity with respect to a hydrogen gas regardless of humidity, but a size of the sensitivity is different according to the humidity. Thus, it can be seen that humidity correction is required to accurately measure a concentration of a hydrogen gas.

<Experimental Example 5> Humidity Measurement Experiment According to the Presence and Absence of Metal-Organic Framework Layer In a photodiode-type battery-free humidity sensor comprising a metal-organic framework layer according to the present inventive concept, in order to see whether the presence or absence of the metal-organic framework layer affects humidity detection, the following experiment was performed.

Specifically, in the photodiode-type battery-free humidity sensors manufactured in Manufacturing Example 2 and Comparative Example 2, while a concentration of moisture was adjusted from 0% to 70%, LED light corresponding to one-twentieth of the sunlight was irradiated onto a chamber to measure a photocurrent using a source meter in real time, thereby measuring gas detection performance of the sensor. Results of the measurement were shown in FIG. 15.

Figure 15:
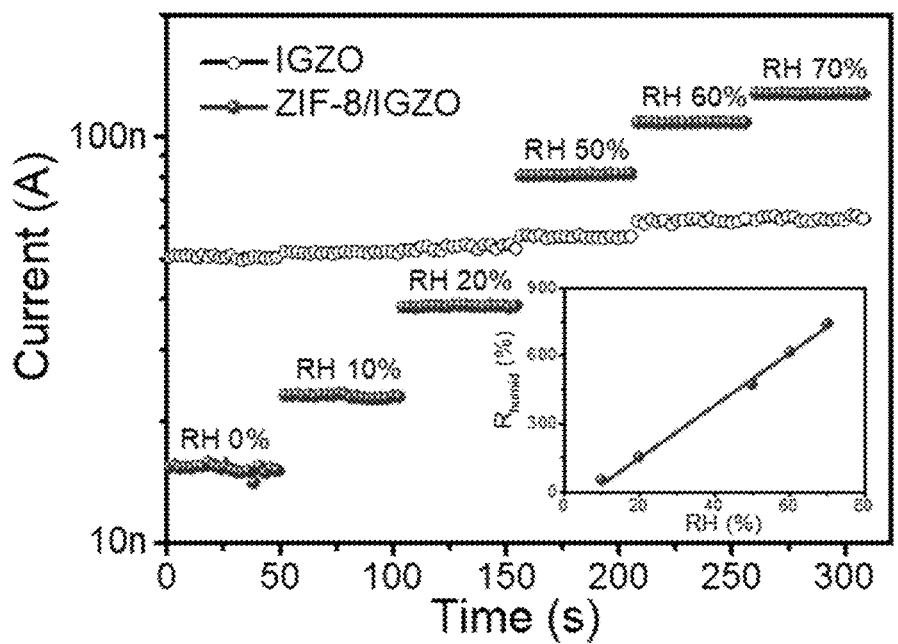
FIG. 15 is a graph showing hydrogen detection performance according to humidity of a photodiode-type battery-free gas sensor according to one example embodiment of the present inventive concept.

As shown in FIG. 15, in the case of the sensor not comprising the metal-organic framework layer, there is little change in current with respect to humidity, but in the case of the sensor comprising the metal-organic framework layer according to the present inventive concept, as humidity is increased, a magnitude of a photocurrent is also increased. Accordingly, when the sensor comprising the metal-organic framework layer according to the present inventive concept does not include a metal nanoparticle catalyst, the metal-organic framework layer may adsorb and detect moisture, and thus, the sensor comprising the metal-organic framework layer may be usefully used as a moisture sensor.

<Experimental Example 6> Measurement of Humidity-Corrected Gas Concentration Through Sensor System According to the Present Inventive Concept A humidity-corrected gas concentration was measured using a sensor system which includes a photodiode-type battery-free gas sensor comprising a metal-organic framework layer and a photodiode-type battery-free humidity sensor comprising a metal-organic framework layer according to the present inventive concept.

Specifically, as shown in FIG. 16, a sensor system comprising the gas sensor (sensor 1) manufactured in Manufacturing Example 1 and the humidity sensor (sensor 2) manufactured in Manufacturing Example 2 on a substrate was introduced into a handmade chamber provided with a mass flow controller (SEC-4550m, Horiba). While a concentration of moisture was adjusted from 10% to 70%, a hydrogen gas having a certain concentration was injected and LED light corresponding to one-twentieth of the sunlight was irradiated onto the chamber to measure a photocurrent using a source meter in real time.

Figure 17:
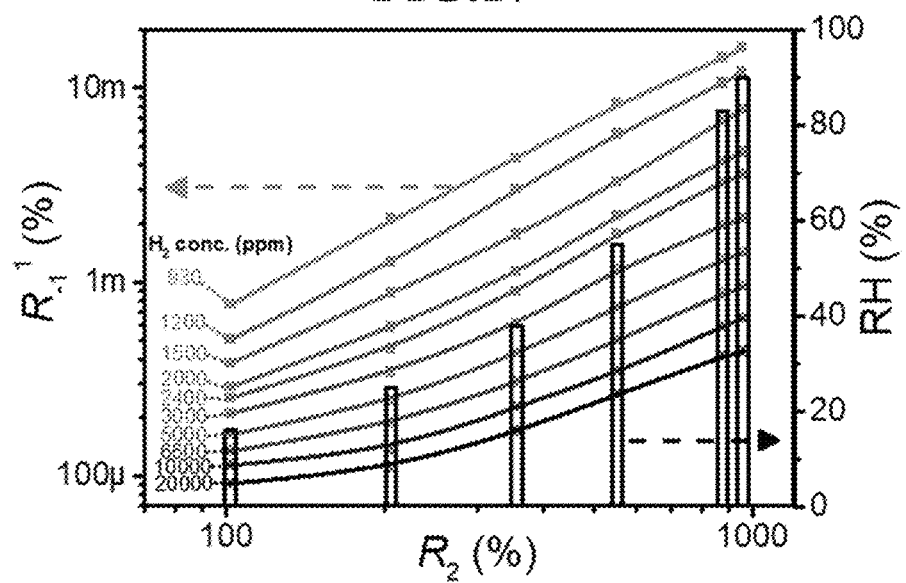
FIG. 17 is a graph showing humidity-corrected hydrogen detection performance in the photodiode-type battery-free gas sensor system in which humidity correction is performed according to still another example embodiment of the present inventive concept.

In the sensor system, sensitivity of sensor 1 was corrected in real time based on a measurement result of sensor 2, and based on a result of the correction, results of the measurement were mapped to coordinates of a reciprocal of the sensitivity of sensor 1 versus the sensitivity of sensor 2 and were shown in FIG. 17.

As shown in FIG. 17, a concentration of detected hydrogen may be accurately measured through a hydrogen concentration graph in which humidity correction is performed.

In a photodiode-type battery-free gas sensor according to the present inventive concept, since photoelectron collection electrodes are formed at regular intervals between P-N junction layers, when light is incident, photoelectrons can be generated in the P-N junction layer and moved to the photoelectron collection electrodes so as to measure a photocurrent without a power source. Since the amount of the photocurrent is changed according to gas adsorption, a gas can be detected through the change in the photocurrent.

In addition, unlike a general system in which a sensor and an element are driven using a solar cell, a photodiode itself can serve as a gas sensor, and thus, there is no need for additional elements for generating, storing, and transmitting energy. Therefore, since the photodiode-type battery-free gas sensor does not include a high-capacity storage device such as a battery, the photodiode-type battery-free gas sensor can be manufactured in a very small size and can be applied in various ways, such as being attached to a portable device such as a smartphone or a smartwatch.

Furthermore, in the photodiode-type battery-free gas sensor according to the present inventive concept, a porous metal-organic framework layer can be formed on metal nanoparticle catalysts to prevent aggregation and surface pollution of the metal nanoparticle catalysts, thereby improving stability, and a target gas can be aggregated in micropores to show an effect of improving sensitivity by eight times or more as compared with when there is no metal-organic framework layer.

In addition, when the catalyst is not attached to the photodiode-type battery-free gas sensor, moisture can be absorbed due to micropores of a metallic-organic framework, the photodiode-type battery-free gas sensor can be used as a humidity sensor.

Therefore, a system that used the photodiode-type battery-free gas sensor and the photodiode-type battery-free humidity sensor together may be performed humidity correction to accurately measure an amount of a gas.

While the present inventive concept has been described with reference to the example embodiments, it should be understood that the present inventive concept is not limited to the example embodiments. The foregoing example embodiments can be made into various alterations and modifications without departing from the scope of the appended claims, and all such alterations and modifications fall within the scope of the present inventive concept. Therefore, the present inventive concept shall be defined by only the claims and their equivalents.

What is claimed is:

1. A photodiode-type battery-free gas sensor comprising:
a semiconductor substrate;
a first insulator layer for an upper electrode which is formed on a part of an upper portion of the semiconductor substrate;
a second insulator layer which is formed on a part of the semiconductor substrate, formed partially in contact with the first insulator layer, formed in a direction perpendicular to a length direction of the first insulator layer, and formed with linear patterns spaced apart from each other by an interval in a range of 5 μm to 30 μm;
photoelectron collection electrodes which are formed on the first insulator layer and the second insulator layer and formed with linear patterns spaced apart from each other by an interval in a range of 5 μm to 30 μm in the same direction as the second insulator layer;
a semiconductor oxide layer which covers a portion or an entirety of each of the photoelectron collection electrodes formed with the linear patterns on the second insulator layer and covers the semiconductor substrate positioned between the linear patterns;
metal nanoparticle catalysts formed on the semiconductor oxide layer;
a metal-organic framework layer formed to cover the semiconductor oxide layer and the metal nanoparticle catalysts;
an upper electrode which covers a portion of each of the photoelectron collection electrodes formed on the first insulator layer so as to be connected to the photoelectron collection electrodes; and
a lower electrode in contact with a lower portion of the semiconductor substrate.

2. The photodiode-type battery-free gas sensor of claim 1, wherein, when the semiconductor substrate is made of a p-type semiconductor material, the semiconductor oxide layer is made of an n-type semiconductor material, and
  when the semiconductor substrate is made of an n-type semiconductor material, the semiconductor oxide layer is made of a p-type semiconductor material.

3. The photodiode-type battery-free gas sensor of claim 2, wherein the p-type semiconductor material is p-type silicon or indium gallium nitride applied to the semiconductor substrate, and
  the n-type semiconductor material is selected from the group consisting of indium gallium zinc oxide (IGZO), zinc oxide (ZnO), tin oxide ($SnO_2$), and titanium dioxide ($TiO_2$) applied as a semiconductor oxide.

4. The photodiode-type battery-free gas sensor of claim 1, wherein the first insulator layer and the second insulator layer are made of silicon oxide or aluminum oxide.

5. The photodiode-type battery-free gas sensor of claim 1, wherein the first insulator layer and the second insulator layer have a thickness ranging from 50 nm to 200 nm.

6. The photodiode-type battery-free gas sensor of claim 1, wherein, when a hydrogen gas is detected, a palladium (Pd) catalyst is used as the metal nanoparticle catalyst,
  when an $NO_2$ gas is detected, a nickel (Ni) catalyst is used as the metal nanoparticle catalyst, and
  when an $H_2S$ gas is detected, a copper (Cu) catalyst is used as the metal nanoparticle catalyst.

7. The photodiode-type battery-free gas sensor of claim 1, wherein a metal constituting the metal-organic framework layer is at least one selected from the group consisting of iron, aluminum, zinc, chromium, zirconium, and copper.

8. The photodiode-type battery-free gas sensor of claim 1, wherein a metal-organic framework constituting the metal-organic framework layer has a specific surface area ranging from 100 $m^2$/g to 4,300 $m^2$/g.

9. The photodiode-type battery-free gas sensor of claim 1, wherein a metal-organic framework constituting the metal-organic framework layer has a density ranging from 0.1 g/$cm^3$ to 1.0 g/$cm^3$.

10. The photodiode-type battery-free gas sensor of claim 1, wherein a metal-organic framework used in the metal-organic framework layer includes at least one selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate).

11. A method of manufacturing a photodiode-type battery-free gas sensor, the method comprising:
  a) forming a first insulator layer for an upper electrode on a part of an upper portion of a semiconductor substrate;
  b) forming a stacked structure of photoelectron collection electrodes and a second insulator layer, which are formed with linear patterns spaced apart from each other by an interval in a range of 5 μm to 30 μm, on the upper portion of the semiconductor substrate comprising the first insulator layer;
  c) forming a semiconductor oxide layer which covers the stacked structure of the photoelectron collection electrodes and the second insulator layer;
  d) forming metal nanoparticle catalysts on the semiconductor oxide layer;
  e) forming a metal-organic framework layer which covers the semiconductor oxide layer and the metal nanoparticle catalysts;
  f) forming an upper electrode which covers the photoelectron collection electrodes formed on the first insulator layer; and
  g) forming a lower electrode below the semiconductor substrate.

12. The method of claim 11, wherein the first insulator layer and the second insulator layer are made of silicon oxide or aluminum oxide.

13. The method of claim 11, wherein the linear patterns of the stacked structure of the photoelectron collection electrodes and the second insulator layer are formed through photolithography.

14. The method of claim 11, wherein a metal-organic framework used in the metal-organic framework layer includes at least one selected from Cu-BTC (copper benzene-1,3,5-tricarboxylate), ZIF-8 (2-methylimidazole zinc salt), MIL-53(AL) (aluminum terephthalate), Fe-BTC (iron 1,3,5-benzenetricarboxylate), KRICT F100 (iron trimesate), KRICT C100 (chromium terephthalate), KRICT C200 (copper trimesate), and KRICT Z100 (zirconium carboxylate).

15. A photodiode-type battery-free humidity sensor comprising:
  a semiconductor substrate;
  a first insulator layer for an upper electrode formed on a part of an upper portion of the semiconductor substrate;
  a second insulator layer which is formed on a part of the semiconductor substrate, formed partially in contact with the first insulator layer, formed in a direction perpendicular to a length direction of the first insulator layer, and formed with linear patterns spaced apart from each other by an interval in a range of 5 μm to 30 μm;
  photoelectron collection electrodes which are formed on the first insulator layer and the second insulator layer and formed with linear patterns spaced apart from each other by an interval in a range of 5 μm to 30 μm in the same direction as the second insulator layer;
  a semiconductor oxide layer which covers a portion or an entirety of each of the photoelectron collection electrodes formed with the linear patterns on the second insulator layer and covers the semiconductor substrate positioned between the linear patterns;
  a metal-organic framework layer which covers the semiconductor oxide layer;
  an upper electrode which covers a portion of each of the photoelectron collection electrodes formed on the first insulator layer so as to be connected to the photoelectron collection electrodes; and
  a lower electrode in contact with a lower portion of the semiconductor substrate.

16. A method of manufacturing a photodiode-type battery-free moisture sensor, the method comprising:
  a) forming a first insulator layer for an upper electrode on a part of an upper portion of a semiconductor substrate;
  b) forming a stacked structure of photoelectron collection electrodes and a second insulator layer, which are formed with linear patterns spaced apart from each other by an interval in a range of 5 μm to 30 μm, on the upper portion of the semiconductor substrate comprising the first insulator layer;
  c) forming a semiconductor oxide layer which covers the stacked structure of the photoelectron collection electrodes and the second insulator layer;
  d) forming a metal-organic framework layer which covers the semiconductor oxide layer;

e) forming an upper electrode which covers the photoelectron collection electrodes formed on the first insulator layer; and g) forming a lower electrode below the semiconductor substrate.

17. A photodiode-type battery-free gas sensor system comprising:

a photodiode-type battery-free gas sensor comprising a semiconductor substrate,
a first insulator layer for an upper electrode formed on a part of an upper portion of the semiconductor substrate,
a second insulator layer which is formed on a part of the semiconductor substrate, formed partially in contact with the first insulator layer, formed in a direction perpendicular to a length direction of the first insulator layer, and formed with linear patterns spaced apart from each other by an interval in a range of 5 µm to 30 µm,
photoelectron collection electrodes which are formed on the first insulator layer and the second insulator layer and formed with linear patterns spaced apart from each other by an interval in a range of 5 µm to 30 µm in the same direction as the second insulator layer,
a semiconductor oxide layer which covers a portion or an entirety of each of the photoelectron collection electrodes formed with the linear patterns on the second insulator layer and covers the semiconductor substrate positioned between the linear patterns,
metal nanoparticle catalysts formed on the semiconductor oxide layer,
a metal-organic framework layer formed to cover the semiconductor oxide layer and the metal nanoparticle catalysts,
an upper electrode which covers a portion of each of the photoelectron collection electrodes formed on the first insulator layer so as to be connected to the photoelectron collection electrodes, and
a lower electrode in contact with a lower portion of the semiconductor substrate; and
a photodiode-type battery-free humidity sensor comprising a semiconductor substrate,
a first insulator layer for an upper electrode formed on a part of an upper portion of the semiconductor substrate,
a second insulator layer which is formed on a part of the semiconductor substrate, formed partially in contact with the first insulator layer, formed in a direction perpendicular to a length direction of the first insulator layer, and formed with linear patterns spaced apart from each other by an interval in a range of 5 µm to 30 µm,
photoelectron collection electrodes which are formed on the first insulator layer and the second insulator layer and formed with linear patterns spaced apart from each other by an interval in a range of 5 µm to 30 µm in the same direction as the second insulator layer,
a semiconductor oxide layer which covers a portion or an entirety of each of the photoelectron collection electrodes formed with the linear patterns on the second insulator layer and covers the semiconductor substrate positioned between the linear patterns,
a metal-organic framework layer formed to cover the semiconductor oxide layer,
an upper electrode which covers a portion of each of the photoelectron collection electrodes formed on the first insulator layer so as to be connected to the photoelectron collection electrodes, and
a lower electrode which is in contact with a lower portion of the semiconductor substrate.

18. The photodiode-type battery-free gas sensor system of claim 17, wherein the gas sensor system measures a concentration of a target gas regardless of humidity by correcting a sensitivity of the gas sensor in real time based on measurement results of the humidity sensor.

* * * * *